US006491702B2

(12) United States Patent  
Heilbrun et al.

(10) Patent No.: US 6,491,702 B2
(45) Date of Patent: Dec. 10, 2002

(54) APPARATUS AND METHOD FOR PHOTOGRAMMETRIC SURGICAL LOCALIZATION

(75) Inventors: Mark Peter Heilbrun, Salt Lake City, UT (US); Paul McDonald, Salt Lake City, UT (US); J. Clayton Wiker, Salt Lake City, UT (US); Spencer Koehler, Salt Lake City, UT (US); William Peters, Salt Lake City, UT (US)

(73) Assignee: Sofamor Danek Holdings, Inc., Memphis, TN (US)

( * ) Notice: Subject to any disclaimer, the term of this patent is extended or adjusted under 35 U.S.C. 154(b) by 0 days.

(21) Appl. No.: 09/865,626

(22) Filed: May 29, 2001

(65) Prior Publication Data

US 2001/0039421 A1 Nov. 8, 2001

Related U.S. Application Data

(60) Division of application No. 09/635,594, filed on Aug. 9, 2000, now abandoned, which is a continuation of application No. 09/513,337, filed on Feb. 25, 2000, now Pat. No. 6,146,390, which is a continuation of application No. 09/173,138, filed on Oct. 15, 1998, now Pat. No. 6,165,181, which is a continuation of application No. 08/801,662, filed on Feb. 18, 1997, now Pat. No. 5,836,954, which is a continuation of application No. 08/145,777, filed on Oct. 29, 1993, now Pat. No. 5,603,318, which is a continuation-in-part of application No. 07/871,382, filed on Apr. 21, 1992, now Pat. No. 5,389,101.

(51) Int. Cl.$^7$ .............................................. A61B 19/00
(52) U.S. Cl. ..................................................... 606/130
(58) Field of Search ...................... 606/130; 128/653.1, 128/630, 303, 653.2; 600/414, 421, 424

(56) References Cited

U.S. PATENT DOCUMENTS 3,821,469 A    6/1974  Whestone et al.

(List continued on next page.)

FOREIGN PATENT DOCUMENTS

DE    2534516    2/1976

(List continued on next page.)

OTHER PUBLICATIONS

Afshar, Farhad, et al., "A three dimensional reconstruction of the human brain stem", J. Neurosurg., vol. 57, No. 4, Oct. 1982, pp. 491–495.

(List continued on next page.)

Primary Examiner—Kevin T. Truong
(74) Attorney, Agent, or Firm—Harness, Dickey & Pierce, P.L.C.

(57) ABSTRACT

A method and apparatus for defining the location of a medical instrument relative to features of a medical workspace including a patient's body region are described. Pairs of two-dimensional images are obtained, preferably by means of two video cameras making images of the workspace along different sightlines which intersect. A fiducial structure is positioned in the workspace for defining a three dimensional coordinate framework, and a calibration image pair is made. The calibration image pair comprises two 2D projections from different locations of the fiducial structure. After the calibration image pair is made, the fiducial structure is removed. A standard projection algorithm is used to reconstruct the 3D framework of the fiducial structure from the calibration image pair. Appropriate image pairs can then be used to locate and track any other feature such as a medical instrument, in the workspace, so long as the cameras remain fixed in their positions relative to the workspace. The computations are desirably performed with a computer workstation including computer graphics capability, image processing capability, and providing a real-time display of the workspace as imaged by the video cameras. Also, the 3D framework of the workspace can be aligned with the 3D framework of any selected volume scan, such as MRI, CT, or PET, so that the instrument can be localized and guided to a chosen feature. No guidance arc or other apparatus need be affixed to the patient to accomplish the tracking and guiding operations.

47 Claims, 6 Drawing Sheets

U.S. PATENT DOCUMENTS

| | | |
|---|---|---|
| D233,265 S | 10/1974 | Walchel |
| 3,868,565 A | 2/1975 | Kuipers |
| 3,963,028 A | 6/1976 | Cooley et al. |
| 3,971,133 A | 7/1976 | Mushabac |
| 3,983,474 A | 9/1976 | Kuipers |
| 4,054,881 A | 10/1977 | Raab |
| 4,058,114 A | 11/1977 | Soldner |
| 4,068,156 A | 1/1978 | Jonnson et al. |
| 4,068,556 A | 1/1978 | Foley |
| 4,071,456 A | 1/1978 | McGee et al. |
| 4,117,337 A | 9/1978 | Staats |
| 4,173,228 A | 11/1979 | Van Steenwyk et al. |
| 4,182,312 A | 1/1980 | Mushabac |
| 4,202,037 A | 5/1980 | Glaser et al. |
| 4,209,254 A | 6/1980 | Reymond |
| 4,228,799 A | 10/1980 | Anichkov et al. |
| 4,259,725 A | 3/1981 | Andrews et al. |
| 4,262,306 A | 4/1981 | Renner |
| 4,287,809 A | 9/1981 | Egli et al. |
| 4,314,251 A | 2/1982 | Raab |
| 4,317,078 A | 2/1982 | Weed et al. |
| 4,341,220 A | 7/1982 | Perry |
| 4,358,856 A | 11/1982 | Stivender et al. |
| 4,360,028 A | 11/1982 | Barbier et al. |
| 4,396,945 A | 8/1983 | DiMatteo et al. |
| 4,398,540 A | 8/1983 | Takemura et al. |
| 4,407,298 A | 10/1983 | Lentz et al. |
| 4,419,012 A | 12/1983 | Stephenson et al. |
| 4,422,041 A | 12/1983 | Lienau |
| 4,457,311 A | 7/1984 | Sorenson et al. |
| 4,465,069 A | 8/1984 | Barbier et al. |
| 4,473,074 A | 9/1984 | Vassiliadis |
| 4,506,676 A | 3/1985 | Duska |
| 4,528,510 A | 7/1985 | Loeffler et al. |
| 4,543,959 A | 10/1985 | Sepponen |
| 4,551,678 A | 11/1985 | Morgan et al. |
| 4,553,285 A | 11/1985 | Sachs et al. |
| 4,571,834 A | 2/1986 | Fraser et al. |
| 4,572,198 A | 2/1986 | Codrington |
| 4,583,538 A | 4/1986 | Onik et al. |
| 4,585,350 A | 4/1986 | Pryer et al. |
| 4,592,252 A | 6/1986 | Patil |
| 4,602,622 A | 7/1986 | Bar et al. |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,638,798 A | 1/1987 | Sheldon et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,659,971 A | 4/1987 | Suzuki et al. |
| 4,660,970 A | 4/1987 | Ferrano |
| 4,662,222 A | 5/1987 | Johnson |
| 4,672,306 A | 6/1987 | Thong |
| 4,673,352 A | 6/1987 | Hansen |
| 4,674,057 A | 6/1987 | Caughman et al. |
| D291,246 S | 8/1987 | Lower |
| 4,686,997 A | 8/1987 | Oloff et al. |
| 4,697,595 A | 10/1987 | Breyer et al. |
| 4,698,777 A | 10/1987 | Toyoda et al. |
| 4,701,047 A | 10/1987 | Eibert et al. |
| 4,701,049 A | 10/1987 | Beckmann et al. |
| 4,705,395 A | 11/1987 | Hageniers |
| 4,705,401 A | 11/1987 | Addleman |
| 4,706,665 A | 11/1987 | Gouda |
| 4,709,156 A | 11/1987 | Murphy et al. |
| 4,721,384 A | 1/1988 | Dietrich et al. |
| 4,721,388 A | 1/1988 | Takagi et al. |
| 4,722,056 A | 1/1988 | Roberts et al. |
| 4,723,544 A | 2/1988 | Moore et al. |
| 4,727,565 A | 2/1988 | Ericson |
| 4,733,661 A | 3/1988 | Palestrant |
| 4,733,662 A | 3/1988 | DeSatnick et al. |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,128 A | 6/1988 | Barlett et al. |
| 4,753,528 A | 6/1988 | Hines |
| 4,761,016 A | 8/1988 | Pryor |
| 4,762,016 A | 8/1988 | Stoughton et al. |
| 4,764,015 A | 8/1988 | Bieringer et al. |
| 4,764,016 A | 8/1988 | Johanasson et al. |
| 4,767,934 A | 8/1988 | Stauffer |
| 4,771,787 A | 9/1988 | Wurster et al. |
| 4,775,235 A | 10/1988 | Hecker et al. |
| 4,776,749 A | 10/1988 | Wanzenberg et al. |
| 4,779,212 A | 10/1988 | Levy |
| 4,782,239 A | 11/1988 | Hirose et al. |
| 4,788,481 A | 11/1988 | Niwa |
| D298,862 S | 12/1988 | Tharp et al. |
| D298,863 S | 12/1988 | Tharp et al. |
| D299,070 S | 12/1988 | Tharp et al. |
| 4,791,934 A | 12/1988 | Brunnett |
| 4,793,355 A | 12/1988 | Crum et al. |
| 4,794,355 A | 12/1988 | Sato et al. |
| 4,803,262 A | 2/1989 | Ohtomo et al. |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Breyer et al. |
| 4,829,373 A | 5/1989 | Leberl et al. |
| 4,835,688 A | 5/1989 | Kimura et al. |
| 4,835,710 A | 5/1989 | Schnelle et al. |
| 4,836,778 A | 6/1989 | Baumrind et al. |
| 4,837,669 A | 6/1989 | Tharp et al. |
| 4,841,967 A | 6/1989 | Chang et al. |
| 4,849,692 A | 7/1989 | Blood |
| 4,862,893 A | 9/1989 | Martinelli |
| 4,875,478 A | 10/1989 | Chen |
| 4,879,668 A | 11/1989 | Cline et al. |
| 4,884,566 A | 12/1989 | Mountz et al. |
| 4,892,545 A | 1/1990 | Day et al. |
| 4,896,673 A | 1/1990 | Rose et al. |
| 4,923,459 A | 5/1990 | Nambu |
| 4,931,056 A | 6/1990 | Ghajar et al. |
| 4,933,843 A | 6/1990 | Scheller et al. |
| 4,943,296 A | 7/1990 | Funakubo et al. |
| 4,945,305 A | 7/1990 | Blood |
| 4,945,914 A | 8/1990 | Allen |
| 4,949,034 A | 8/1990 | Imura et al. |
| 4,951,653 A | 8/1990 | Fry et al. |
| 4,954,043 A | 9/1990 | Yoshida et al. |
| 4,955,891 A | 9/1990 | Carol |
| 4,961,422 A | 10/1990 | Marchosky et al. |
| 4,977,655 A | 12/1990 | Martinelli |
| 4,982,188 A | 1/1991 | Fodale et al. |
| 4,991,579 A | 2/1991 | Allen |
| 5,005,142 A | 4/1991 | Lipchak et al. |
| 5,005,578 A | 4/1991 | Greer et al. |
| 5,016,639 A | 5/1991 | Allen |
| 5,017,139 A | 5/1991 | Mushabac |

| Patent No. | Date | Inventor |
|---|---|---|
| 5,027,818 A | 7/1991 | Bova et al. |
| 5,031,203 A | 7/1991 | Trecha |
| 5,037,374 A | 8/1991 | Carol |
| 5,039,867 A | 8/1991 | Nishihara et al. |
| 5,047,036 A | 9/1991 | Koutrouvelis |
| 5,050,608 A | 9/1991 | Watanabe et al. |
| 5,057,095 A | 10/1991 | Fabian |
| 5,059,789 A | 10/1991 | Salcudean et al. |
| 5,070,454 A | 12/1991 | Griffith |
| 5,078,140 A | 1/1992 | Kwoh |
| 5,078,142 A | 1/1992 | Sizcek et al. |
| 5,079,699 A | 1/1992 | Tuy et al. |
| 5,080,662 A | 1/1992 | Paul |
| 5,086,401 A | 2/1992 | Glassman et al. |
| 5,094,241 A | 3/1992 | Allen |
| 5,097,839 A | 3/1992 | Allen |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,119,817 A | 6/1992 | Allen |
| 5,142,930 A | 9/1992 | Allen et al. |
| 5,143,076 A | 9/1992 | Hardy et al. |
| 5,150,715 A | 9/1992 | Ishiguro et al. |
| 5,161,536 A | 11/1992 | Vilkomerson et al. |
| 5,163,430 A | 11/1992 | Carol |
| 5,166,875 A | 11/1992 | Machida |
| 5,178,146 A | 1/1993 | Giese |
| 5,178,164 A | 1/1993 | Allen |
| 5,186,174 A | 2/1993 | Schlöndorff et al. |
| 5,187,475 A | 2/1993 | Wagener et al. |
| 5,188,126 A | 2/1993 | Fabian et al. |
| 5,189,690 A | 2/1993 | Samuel |
| 5,190,059 A | 3/1993 | Fabian et al. |
| 5,193,106 A | 3/1993 | DeSena |
| 5,197,476 A | 3/1993 | Nowacki et al. |
| 5,198,877 A | 3/1993 | Schulz |
| 5,207,223 A | 5/1993 | Adler |
| 5,211,164 A | 5/1993 | Allen |
| 5,211,165 A | 5/1993 | Dumoulin et al. |
| 5,214,615 A | 5/1993 | Bauer |
| 5,222,499 A | 6/1993 | Allen et al. |
| 5,224,049 A | 6/1993 | Mushabac |
| 5,230,338 A | 7/1993 | Allen et al. |
| 5,230,623 A | 7/1993 | Guthrie et al. |
| 5,243,984 A | 9/1993 | Ogura et al. |
| 5,249,581 A | 10/1993 | Horbal et al. |
| 5,251,127 A | 10/1993 | Raab |
| 5,253,647 A | 10/1993 | Takahashi et al. |
| 5,255,680 A | 10/1993 | Darrow et al. |
| 5,257,629 A | 11/1993 | Kitney et al. |
| 5,257,998 A | 11/1993 | Ota et al. |
| 5,261,404 A | 11/1993 | Mick et al. |
| 5,265,610 A | 11/1993 | Darrow et al. |
| 5,271,400 A | 12/1993 | Dumoulin et al. |
| 5,273,025 A | 12/1993 | Sakiyama et al. |
| 5,273,039 A | 12/1993 | Fujiwara et al. |
| 5,274,551 A | 12/1993 | Corby, Jr. |
| 5,279,309 A | 1/1994 | Taylor et al. |
| 5,285,787 A | 2/1994 | Machida |
| 5,291,889 A | 3/1994 | Kenet et al. |
| 5,295,200 A | 3/1994 | Boyer |
| 5,295,483 A | 3/1994 | Nowacki et al. |
| 5,299,254 A | 3/1994 | Dancer et al. |
| 5,299,288 A | 3/1994 | Glassman et al. |
| 5,305,091 A | 4/1994 | Gelbart et al. |
| 5,305,203 A | 4/1994 | Raab |
| 5,309,913 A | 5/1994 | Kormos et al. |
| 5,315,630 A | 5/1994 | Sturm et al. |
| 5,318,025 A | 6/1994 | Dumoulin et al. |
| 5,329,944 A | 7/1994 | Fabian et al. |
| 5,332,971 A | 7/1994 | Aubert |
| D349,573 S | 8/1994 | Bookwalter et al. |
| 5,345,087 A | 9/1994 | Luber et al. |
| 5,345,938 A | 9/1994 | Nishiki et al. |
| 5,353,795 A | 10/1994 | Souza et al. |
| 5,355,129 A | 10/1994 | Baumann |
| 5,357,953 A | 10/1994 | Merrick et al. |
| 5,359,417 A | 10/1994 | Müller et al. |
| 5,368,030 A | 11/1994 | Zinreich et al. |
| D353,668 S | 12/1994 | Banks et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,389,101 A | 2/1995 | Heilbrun et al. |
| 5,391,199 A | 2/1995 | Ben-Haim |
| 5,394,457 A | 2/1995 | Leibinger et al. |
| 5,397,329 A | 3/1995 | Allen |
| 5,398,684 A | 3/1995 | Hardy |
| 5,399,146 A | 3/1995 | Nowacki et al. |
| 5,399,951 A | 3/1995 | Lavallee et al. |
| D357,534 S | 4/1995 | Hayes |
| 5,402,801 A | 4/1995 | Taylor |
| 5,408,409 A | 4/1995 | Galssman et al. |
| 5,413,573 A | 5/1995 | Koivukangas |
| D359,557 S | 6/1995 | Hayes |
| 5,423,334 A | 6/1995 | Jordan |
| 5,425,367 A | 6/1995 | Shapiro et al. |
| 5,425,382 A | 6/1995 | Golden et al. |
| 5,429,132 A | 7/1995 | Guy et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,445,150 A | 8/1995 | Dumoulin et al. |
| 5,446,548 A | 8/1995 | Gerig et al. |
| 5,447,154 A | 9/1995 | Cinquin et al. |
| 5,453,686 A | 9/1995 | Anderson |
| 5,456,718 A | 10/1995 | Szymaitis |
| 5,480,422 A | 1/1996 | Bein-Haim |
| 5,483,961 A | 1/1996 | Kelly et al. |
| 5,490,196 A | 2/1996 | Rudich et al. |
| 5,494,034 A | 2/1996 | Schöndorff et al. |
| 5,513,637 A | 5/1996 | Twiss et al. |
| 5,515,160 A | 5/1996 | Schulz et al. |
| 5,515,853 A | 5/1996 | Smith et al. |
| 5,517,990 A | 5/1996 | Kalfas et al. |
| 5,526,576 A | 6/1996 | Fuch et al. |
| 5,531,227 A | 7/1996 | Schneider |
| 5,531,520 A | 7/1996 | Grimson et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,564,437 A | 10/1996 | Bainville et al. |
| 5,568,809 A | 10/1996 | Ben-Haim |
| 5,575,798 A | 11/1996 | Koutrouvelis |
| 5,588,430 A | 12/1996 | Bova et al. |
| 5,590,215 A | 12/1996 | Allen |
| 5,592,939 A | 1/1997 | Martinelli |
| 5,595,767 A | 1/1997 | Cinquin et al. |
| 5,600,330 A | 2/1997 | Blood |
| 5,603,318 A | 2/1997 | Heilbrun et al. |
| 5,622,169 A | 4/1997 | Golden et al. |
| 5,622,170 A | 4/1997 | Schulz |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwarign et al. |
| 5,640,170 A | 6/1997 | Anderson |
| 5,645,065 A | 7/1997 | Shapiro et al. |

| | | | | | |
|---|---|---|---|---|---|
| 5,647,361 A | 7/1997 | Damadian | | FOREIGN PATENT DOCUMENTS | |
| 5,662,111 A | 9/1997 | Cosman | | | |
| 5,676,673 A | 10/1997 | Ferre et al. | DE | 28 31 278 | 2/1979 |
| 5,682,886 A | 11/1997 | Delp et al. | DE | 2852949 | 6/1980 |
| 5,682,890 A | 11/1997 | Kormos et al. | DE | 3205085 | 9/1983 |
| 5,690,108 A | 11/1997 | Chakeres | DE | 3508730 | 3/1985 |
| 5,694,945 A | 12/1997 | Ben-Haim | DE | 3508730 A1 | 9/1986 |
| 5,695,500 A | 12/1997 | Taylor et al. | DE | 8701668 | 5/1987 |
| 5,695,501 A | 12/1997 | Carol et al. | DE | 3831278 | 3/1989 |
| 5,697,377 A | 12/1997 | Wittkampf | DE | 3904595 | 4/1990 |
| 5,715,822 A | 2/1998 | Watkins et al. | DE | 3902249 | 8/1990 |
| 5,727,552 A | 3/1998 | Ryan | DE | 3838011 | 2/1991 |
| 5,727,553 A | 3/1998 | Saad | DE | 3717871 | 2/1993 |
| 5,729,129 A | 3/1998 | Acker | DE | 3205915 | 9/1993 |
| 5,730,129 A | 3/1998 | Darrow et al. | DE | 4225112 | 12/1993 |
| 5,732,703 A | 3/1998 | Kalfas | DE | 19832296 | 2/1996 |
| 5,740,801 A | 4/1998 | Branson | DE | 4432890 | 5/1997 |
| 5,740,802 A | 4/1998 | Nafis et al. | DE | 19751761 | 10/1998 |
| 5,742,394 A | 4/1998 | Hansen | EP | 0 155 857 | 9/1985 |
| 5,744,953 A | 4/1998 | Hansen | EP | 0 207 452 | 1/1987 |
| 5,745,545 A | 4/1998 | Hughes | EP | 0 359 773 B1 | 5/1988 |
| 5,748,767 A | 5/1998 | Raab | EP | 0 322 363 | 6/1989 |
| 5,749,362 A | 5/1998 | Funda et al. | EP | 0 326 768 A2 | 8/1989 |
| 5,752,513 A | 5/1998 | Acker et al. | EP | 0 427 358 A1 | 5/1991 |
| 5,755,725 A | 5/1998 | Druais | EP | 0 456 103 A2 | 11/1991 |
| RE35,816 E | 6/1998 | Schulz | EP | 0 469 966 A1 | 2/1992 |
| 5,758,667 A | 6/1998 | Slettenmark | EP | 0 581 704 A1 | 2/1994 |
| 5,762,064 A | 6/1998 | Polvani | EP | 0603089 | 6/1994 |
| 5,767,669 A | 6/1998 | Hansen et al. | EP | 0 501 993 B1 | 6/1997 |
| 5,767,960 A | 6/1998 | Orman | EP | 0655138 | 4/1998 |
| 5,769,789 A | 6/1998 | Wang et al. | EP | 0860144 | 8/1998 |
| 5,769,843 A | 6/1998 | Abela et al. | EP | 0894473 | 2/1999 |
| 5,769,861 A | 6/1998 | Vilsmeier | EP | 0908146 | 4/1999 |
| 5,772,594 A | 6/1998 | Barrick | EP | 0919202 | 6/1999 |
| 5,776,064 A | 7/1998 | Kalfas | EP | 0919203 | 6/1999 |
| 5,782,765 A | 7/1998 | Jonkman | EP | 0930046 | 7/1999 |
| 5,787,886 A | 8/1998 | Kelly et al. | EP | 0934730 | 8/1999 |
| 5,795,294 A | 8/1998 | Luber et al. | FR | 359773 B1 | 2/1979 |
| 5,797,849 A | 8/1998 | Vesely et al. | FR | 2 417 970 | 10/1979 |
| 5,799,055 A | 8/1998 | Peshkin et al. | GB | 2094590 | 9/1982 |
| 5,799,099 A | 8/1998 | Wang et al. | JP | 62-000327 | 6/1987 |
| 5,800,352 A | 9/1998 | Ferre et al. | WO | WO 96/11624 | 4/1966 |
| 5,807,387 A | 9/1998 | Druais | WO | WO 88/09151 | 12/1988 |
| 5,810,728 A | 9/1998 | Kuhn | WO | WO 90/05494 | 5/1990 |
| 5,820,553 A | 10/1998 | Hughes | WO | WO 91/04711 | 4/1991 |
| 5,823,958 A | 10/1998 | Truppe | WO | WO 91/07726 | 5/1991 |
| 5,828,770 A | 10/1998 | Leis et al. | WO | WO 92/00702 | 1/1992 |
| 5,829,444 A | 11/1998 | Ferre et al. | WO | WO 92/06645 | 4/1992 |
| 5,831,260 A | 11/1998 | Hansen | WO | WO 92/10439 | 11/1992 |
| 5,833,608 A | 11/1998 | Acker | WO | WO 93/10710 | 6/1993 |
| 5,836,954 A | 11/1998 | Heilburn et al. | WO | WO 93/20528 | 10/1993 |
| 5,848,967 A | 12/1998 | Cosman | WO | WO 94/23647 | 10/1994 |
| 5,851,183 A | 12/1998 | Bucholz | WO | WO 94/24933 | 11/1994 |
| 5,868,675 A | 2/1999 | Henrion et al. | WO | WO 95/07055 | 3/1995 |
| 5,871,445 A | 2/1999 | Bucholz | WO | WO 95/25475 | 9/1995 |
| 5,873,822 A | 2/1999 | Ferre et al. | WO | WO 96/32059 | 10/1996 |
| 5,891,034 A | 4/1999 | Bucholz | WO | WO 97/36192 | 10/1997 |
| 5,907,395 A | 5/1999 | Schulz et al. | WO | WO 97/40764 | 11/1997 |
| 5,913,820 A | 6/1999 | Bladen et al. | WO | WO 98/38908 | 9/1998 |
| 5,920,395 A | 7/1999 | Schulz | WO | WO 99/15097 | 4/1999 |
| 5,957,844 A | 9/1999 | Dekel et al. | WO | WO 99/21498 | 5/1999 |
| 5,971,997 A | 10/1999 | Guthrie et al. | WO | WO 99/23946 | 5/1999 |
| 5,987,349 A | 11/1999 | Schulz | WO | WO 99/23956 | 5/1999 |
| 5,999,840 A | 12/1999 | Grimson et al. | WO | WO 99/26549 | 6/1999 |
| 6,006,126 A | 12/1999 | Cosman | WO | WO 99/27839 | 6/1999 |
| 6,016,439 A | 1/2000 | Acker | WO | WO 99/29253 | 6/1999 |
| 6,019,725 A | 2/2000 | Vesely et al. | WO | WO 99/33406 | 7/1999 |
| 6,094,007 A | 7/2000 | Faul et al. | WO | WO 99/38449 | 8/1999 |
| 6,146,390 A | 11/2000 | Heilbrun et al. | WO | WO 99/52094 | 10/1999 |
| 6,167,295 A * | 12/2000 | Cosman ............ 600/414 | WO | WO 99/60939 | 12/1999 |
| 6,175,756 B1 * | 1/2001 | Ferre et al. ............ 600/424 | | | |

OTHER PUBLICATIONS

Apuzzo, M.L.J. et al., "Computed Tomographic Guidance Sterotaxis in the Management of Intracranial Mass Lesions", Neurosurgery, vol. 12, No. 3, 1983, pp. 227–285.

Arun, K.S., et al., "Transactions on Pattern Analysis and machine Intelligence, " IEEE , vol. PAMI–9, No. 5, 1987, pp. 698–770.

Awwad, Eric E., et al., "Post–Traumatic Spinal Synovial Cyst with Spondylolysis CT Features," Journal of computer Assisted Tomography, vol. 13, No. 2, pp. 334–337, Mya/Apr. 1989.

Awwad, Eric E., et al., "MR Imaging of Lumar Juxtaarticular Cysts," Journal of Computer Assisted Tomography, vol. 14, No. 3, pp. 415–417, Mar./Jun. 1990.

Bajcsy, Ruzena, et al., "Computerized Anatomy Atlas of the Human Brain," Proceedings fo the Second Annual Conference & Exhibition of The National Computer Graphics Association, Inc., Jun. 14–18, 1981, pp. 435–441.

Balter, James M., et al., "Correlation of projection radiographs in radiation therapy using open curve segments and points," Med Phys. 19 (2), Mar./Apr. 1992, pp. 329–334.

Barnett, G.H. et al., "Armless Wand for Accurate Frameless Sterotactic Surgical Localization," Poster #1119, Scientific Program, 1992 Annual Meeting, American Association of Neurological surgeons, San Francisco, CA, Apr. 11–16, 1992, pp. 284–285.

Batnitzky, Solomon, M.D., et al., "Three–Dimensional Computer Reconstruction of Brain Lesions from Surface Contours Provided by Computed Tomography: A Prosepctus," Neurosurgery, vol. 11, No. 1, Jul. 1982, pp. 73–84.

Benzel, Edward C., et al., "Magnetic source Imaging: A Review of the Magnes System of Biomagnetic Technologies Incorporated, " Neurosurgery, vol. 33, No. 2, pp. 252–259, Aug. 1993.

Bergström, Mats, et al., "Stereotaxic Computed Tomography," Am. J. Roentgenol. 127:167–170, 1976, pp. 167–170.

Birg, W., et al., "A Computer Programme System for Sterotactic Neurosurgery," Acta Neurochirugica Suppl., 24, 1977, 99–108.

Boëthius, J., et al., "Sterotaxic Computerized Tomography With a GE 8800 Scanner," J. Neurosurg. vol. 52, Jun. 1980, pp. 794–800.

Boëthius, J., et al., "Stereotaxic Biopsies and Computer Tomography in Gliomas," Acta Neurochirurgica, vol. 40, Fasc. 3–4, 1978, pp. 223–232.

Bopp, H., "An Orientation and Calibration Method for Non–Toxographic Applications," Photogrammetric Engineering and Remote Sensing, vol. 44, No. 9, Sep. 1978, pp. 1191–1196.

Brown, Russell, A., "A Sterotactic Head Frame for Use with CT Body Scanners," Inv. Radiol., vol. 14, No. 4, pp. 300–304, Jul.–Aug. 1979.

Brown, Russell, A., M.D., "A Computerized Tomography –Computer Graphics Approach to Sterotaxic Localization," J. Neurosurg, vol. 50, No. 6, 1979, pp. 715–720.

Bucholz, Richard D., et al., "Halo Vest Versus Spinal Fusion for Cervical Injury: Evidence From an Outcome Study," J. Neurosurg., vol. 70, No. 6, pp. 884–892, Jun. 1989.

Bucholz, Richard D. et al., "Armless Wand for Accurate Frameless Stereotactic Surgical Localization," American Association of Neurological Surgeons, 1992 Annual Meeting, pp. 284–285, poster 1120.

Bucholz, Richard D., "The Central Sulcus and Surgical Planning," AJNR, vol. 14, pp. 926–927, Jul./Aug. 1993.

Bucholz, Dr. Richard D., Declaration of Richard D. Bucholz, pp. 1–4, with attached Exhibits A (pp. 1–29) and B (pp. 1–2), Dec. 23, 1997.

Bucholz, Richard D., et al., "Intraoperative Localization Using a Three Dimensional Optical Digitizer," Proceedings of Clinical Applications of Modern Imaging Technology, SPIE, vol. 1894, The International Society of Optical Engineering, pp. 312–322, Jan. 17–19, 1993.

Bucholz, Richard D. et al., "A Comparison of Sonic Digitizers Versus Light Emitting Diode–Based Localization," Interactive Image–Guided Neurosurgery, Chapter 16, pp. 179–200.

Bucholz, R.D., et al., "Use of an Intraoperative Optical Digitizer in a System for Free–Hand Stereotactic Surgery," Poster #1120, Scientific Program, 1992 Annual Meeting, American Association of Neurological Surgeons, San Francisco, CA, Apr. 11–16, 1992, pp. 284–285.

Bullard, D.E., et al., "C.T.–Guided Stereotactic Biopsies Using a Modified Frame and Gildenberg Techniques," Neurology, Neurosurgery, and Psychiatry, vol. 47, pp. 509–595, 1984.

Byte Magazine, "3–D Digitizer Captures the World" (Oct. 1990), p. 43.

Castleman, Kenneth R., "Digital Image Processing," Prentice Hall, Inc., 1979, pp. 364–369.

Champleboux, "Utilisation De Fonctions Splines Pour La Mise Au Point d'Un Capteur Tridimension Sans Contact," Theses, Docteur de L'Univerite' Joseph Fourie Grenoble Jul. 1, 1991.

Champleboux, et al., "Accurate Calibration of Cameras and Range Imaging Sensors: the NPBS Method," 1992, 6 pages.

Cinquin, et al., "IGOR: Image Guided Operating Robot, Methodology, Applications,"IEEE EMBS, Paris, 1992 pp. 1–2.

Cinquin, et al., "Computer Assisted Medical Interventions," The 1.sup.st Workshop on Domestic Robotics—The 2.sup.nd Workshop on Medical & Healthcare Robotics, Sep. 5–7, 1989, pp. 63–65.

Clarysse, Patrick, et al., "A Computer–Assisted System for 3–D Frameless Localization in Stereotaxic MRI," IEEE Transaction on Medical Imaging, vol. 10, No. 4, pp. 523–529, Dec. 1991.

Colchester, et al., "Information Processing in Medical Imaging," Lecture Notes in Computer Science, Jul. 1991, pp. 51–58.

Dever, Bill and S. James Zinreich, M.D., "OR role seen for 3–D imaging," Radiology Today, 2 pages, Feb. 1991.

Foley, J.D., et al., "Geometrical Transformations," Fundamentals of Interactive Computer Graphics, The System Programming Series, Addison–Wesley Publishing Company, 1982, pp. 245–266.

Friets, et al., "A Frameless Sterotaxic Operating Microscope for Neurosurgery", IEEE Transactions on Biomedical Engineering, vol. 36, No. 6 (Jun. 1989), pp. 608, 613–617.

Gallen, Christopher C., et al., "Intracranial Neurosurgery Guided by Functional Imaging," Surg. Neurol., vol. 42, pp. 523–530, 1994.

Galloway, Jr., Robert L., et al., "Interactive Image–Guided Neurosurgery," IEEE Transactions on Biomedical Engineering, vol. 39, No. 12, pp. 1226–1331, Dec. 1992.

Gildenberg, Philip L., M.D., et al., "Calculation of Stereotactic Coordinates from the Computed Tomographic Scan," Neurosurgery, vol. 10, No. 5, May 1982, pp. 580–586.

Glaser, Edmund M. et al., "The Image–Combining Computer Microscope—an Interactive Instrument for Morphometry of the Nervous System," Journal of Neuroscience Methods, vol. 8, pp. 17–32, 1983.

Gleason, Curtis A., Ph.D., et al., "Stereotactic Localization (with Computerized Tomographic Scanning), Biopsy, and Radiofrequency Treatment of Deep Brain Lesions," Neurosurgery, vol. 2, No. 3, 1978, pp. 217–222.

Gomez, Camilo R., et al., "Transcranial Doppler Ultrasound Following Closed Head Injury: Vasospasm or Vasoparalysis?," Surg. Neurol., vol. 35, No. 1, pp. 30–35, Jan. 1991.

Gonzalez, Rafael C., et al., "Digital Image Fundamentals," Digital Imaging Processing Second Edition, Addison–Wesley Publishing Company, 1987, pp. 52–54.

Gouda, Kasim I., M.D., et al., "New frame for stereotaxic surgery," J. Neurosurg. vol. 53, Aug. 1980, pp. 259–259.

Greitz, T., et al., "Head Fixation System for Integration of Radiodiagnostic and Therapeutic Procedures," Neuroradiology, vol. 19, No. 1, 1980, pp. 1–6.

Hahn, Joseph F., M.D., et al., "Needle Biopsy of Intracranial Lesions Guided by Computerized Tomography," Neurosurgery, vol. 5, No. 1, 1979, pp. 11–15.

Hanson, Gayle, "Robots Roll into Operating Rooms," Insight, Apr. 8, 1991, pp. 44–45.

Hatch, John F., "Reference–Display System for the Integration of CT Scanning and the Operating Microscope," Dartmouth College, Oct. 1984, entire thesis.

Hatch, J.F., et al., "Reference–Display System for the Integration of CT Scanning and the Operating Microscope," Proceedings of the Eleventh Annual Northeast Bioengineering Conference, Mar. 14–15, 1985, IEEE 1985, pp. 252–254.

Heilbrun, M. Peter, MD, "Progressive Technology Applications," Neurosurgery for the Third Millenium, Ch. 15, pp. 191–198.

Heilbrun, M. Peter, MD, et al. "Stereotactic Localization and Guidance Using a Machine Vision Technique," Proceedings of the Meeting of the American Society for Stereotactic and Functional Neurosurgery, Pittsburgh, PA, Jun. 16–19, 1991 Sterotact Funct Neurosurg; 58:94–98.

Heilbrun, M. Peter, et al., "Preliminary Experience with a Brown–Roberts–Wells (BRW) Computerized Tomography Stereotaxic Guidance System," J. Neurosurg., vol. 59, pp. 217–222, Aug. 1983.

Heilbrun, M. Peter, MD, Declaration of Dr. Mark P. Heilbrun, 3 pages, dated Nov. 19, 1999.

Heilbrun, M. Peter, M.D., "Computed Tomography–Guided Stereotactic Systems," Clinical Neurosurgery, Chapter 31.

Henderson, Jaime M., et al., "An Accurate and Ergonomic Method of Registration for Image–Guided Neurosurgery," Computerized Medical Imaging and Graphics, vol. 18, No. 4, pp. 273–277, 1994.

Hinck, M.D., Vincent C., et al., "A precise technique for craniotomy localization using computerized tomography," J. Neurosurg, vol. 54, No. 3, Mar. 1981, pp. 416–418.

Hoerenz, Peter, "The Operating Microscope, I., Optical Principles, Illumination Systems, and Support Systems," Journal of Microsurgery, vol. 1, No. 5, Mar.–Apr. 1980, pp. 364–369.

Holman, B. Leonard, et al., "Correlation of projection radiographs in radiation therapy using open curve segments and points," Med. Phys. 19 (2), Mar./Apr. 1992, pp. 329–334.

Holman, B. Leonard, et al., "Computer–Assisted Superimposition of Magnetic Resonance and High–Resolution Technetium–99–m–HMPAO and Thallium–201 SPECT Images of the Brain," The Journal of Nuclear Medicine, vol. 32, No. 8, Aug. 1991, pp. 1478–1484.*

Horner, M.D., Neil B., et al., "A Comparison of CT–Stereotaxic Brain Biopsy Techniques," Investigative Radiology, vol. 19, Sep.–Oct. 1984, pp. 367–373.*

Hounsfield, G.N., "Computerized transverse axial scanning (tomography): Part 1., Description of Ssytem," British Journal of Radiology, vol. 46, 1973, pp. 1016–1022.*

Jacques, Skip, M.D., et al., "A Computerized Microstereotactic Method to Approach, 3–Dimensionally Reconstruct, Remove and Adjuvantly Treat Small CNS Lesions," Appl. Neurophysiology 43:176–182, 1980.*

Jacques, Skip, M.D., et al., "Computerized three–dimensional stereotaxic removal of small central nervous system lesions in patients," J. Neurosurg, vol. 53, No. 6, Dec. 1980, pp. 816–820.*

Johnson, H., "The Mechanical Engineer and the Transition To Image Analysis," Advanced Imaging, Nov. 1990, pp. 52–56.*

Kato, et al., "A Frameless, Armless Navigational System for Computer Assisted Neurosurgery" 74 J. Neurosurg, 845–49, 1991.*

Kaufman, Howard H., M.D., "New Head–positioning System for Use with Computed Tomographic Scanning," Neurosurgery, vol. 7, No. 2, Aug. 1980, pp. 147–149.*

Kelly, Patrick J., M.D., et al. "A Microstereotactic Approach to Deep–seated Arteriovenous Malformations," Surgical Neurology, vol. 17, No. 4, Apr. 1982, pp. 260–262.*

Kelly, Patrick J., "Instrumentation, Technique and Technology," Neurosurgery, vol. 37, No. 2, pp. 348–350, Aug. 1995.*

Kelly, P.J., et al., "Precision Resection of Intra–Axial CNS Lesions by CT–Based Stereotactic Craniotomy and Computer Monitored $CO_2$ Laser," Acta Neurochirurgica, vol. 68, 1983, pp. 1–9.*

Kelly, Patrick J., et al., "Stereotactic CT Scanning for the Biopsy of Intracranial Lesions and Functional Neurosurgery," Applied Neurophysiology, vol. 46, Dec. 1983, pp. 193–199.*

Kelly, M.D., Patrick J., et al., "A Stereotactic Approach to Deep–Seated Central Nervous System Neoplasms Using the Carbon Dioxide Laser," Surgical Neurology, vol. 15, No. 5, May 1981, pp. 331–334.

Kelly, Patrick J., M.D., et al., "Computer–Assisted Stereotaxic Laser Resection of Intra–Axial Brain Neoplasma," J. Neurosurg., vol. 64, Mar. 1976, pp. 427–439.

Klimek, "Long–Term Experience with Different Types of Localization Systems in Skull–Base Surgery," Erar, Nose, and Throat Surgery, vol. 51, pp. 635–638.

Kosugi, Yukio, et al., "An Articulated Neurosurgical Navigation System Using MRI and CT Images," IEEE Transaction on Biomedical Engineering, vol. 35, No. 2, Feb. 1988, pp. 147–152.

Krybus, W. et al., "Navigation Support for Surgery by Means of Optical Position Detection," Proceedings of CAR '91, pp. 362–366.

Laitinen, Lauri V., M.D., "Trigeminus Stereoguide: An Instrument for Stereotactic Approach Through the Foramen Ovale and Foramen Jugulare," Surg. Neurol., vol. 22, pp. 519–523, 1984.

Lavalee, et al., "Matching of Medical Images for Computed and Robot Assisted Surgery," 2 pp.

Lavalee, "A New System for Computer Assisted Neurosurgery," IEEE Engineering in Medicine & Biology Society 11.sup.th Annual International Conference, 1989.

Lavalee, et al., "Computer Assisted Interventionist Imaging: The Instance of Stereotactic Brain Surgery," Medinfo, 1989, pp. 613–617.

Lavalee, et al., "Computer Assisted Driving of a Needle into the Brain," Computer Assisted Radiology, 1989, pp. 416–420.

Lavalee, S., et al., "Matching 3–D Smooth Surfaces with Their 2–D Projections using 3–D Distance Maps," SPIE, vol. 1570, Geometric Methods in Computer Vision, (1991), pp. 322–336.

Lavalee, et al., "Computer Assisted Medical Interventions," NATO ASI 1990, pp. 301–312, vol. F60.

Lavalee, et al., "Ponction Assistee Par Ordinateur" ("Computer Assisted Puncture"), afcet INRIA, Nov. 1987, pp. 439–449.

Lavalee, et al., "Vi Adaptation de la Methodologie A Quelques Applications Cliniques," undated, pp. 133–148.

Leavitt, Dennis D. Ph.D., et al., "Dynamic Field Shaping to Optimize Stereotactic Radiosurgery," Int. J. Radiation Oncology Biol. Phys., vol. 21, pp. 1247–1255.

Leksell, L., et al., "Stereotaxis and Tomography, A Technical Note," Acta Neurochirurgica, vol. 52, Fasc–1–2, 1980, pp. 1–7.

Levin, David N., et al., "The Brain: Integrated Three–dimensional Display of MR and PET Images," Radiology, Sep. 1989, vol. 172, No. 3, pp. 783–789.

Levin, D., et al., "Multimodality 3–D View of the Brain Created from MRI and PET Scans," SMRI 1989: Seventh Annual Meeting Program and Abstracts, vol. 7, Supplement 1, p. 89.

Levinthal, Robert, M.D., et al., "Techniques for Accurate Localization with the CT–Scanner," Bulletin of the Los Angeles Neurological Societies, vol. 41, No. 1, Jan. 1976, pp. 6–8.

Lunsford, L. Dade, M.D., "Innovations in Stereotactic Technique Couple with Computerized Tomography," Contemporary Neurosurgery, 1982, pp. 1–6.

MacFarlane, John R., M.D., et al., "Neurosurgery Image Manager," Neurosurgery, vol. 29, No. 2, Aug. 1991, pp. 309–314.

MacKay, Alexander R., M.D., et al., "Computed Tomography–directed Stereotaxy for Biopsy and Interstitial Irradiation of Brain Tumors: Technical Note," Neurosurgery, vol. 11, No. 1, 1982, pp. 38–42.

Maroon, Joseph C., M.D., et al., "Intracranial biopsy assisted by computerized tomography," J. Neurosurg., vol. 46, No. 6, Jun. 1977, pp. 740–744.

Mazier, et al., "Computer Assisted Vertebral Column Surgery: application to the Spinal Pedicle Fixation," Innov. Tech. Biol. Med., vol. 11, No. 5, 1990, pp. 559–565.

Mazier, B., et al., "Computer Assisted Vertebral Column Surgery: Application to the Spinal Pedical Fixation," Innovation et Technologie en Biologie et Medecine, pp. 559–566.

Mazier, et al., "Computer Assisted Interventionist Imaging: Application to the Vertebral Column Surgery," IEEE, vol. 12, No. 1, 1990, pp. 430–431.

Mesqui, F., et al., "Real–Time, Nonivasive Recording and Three–Dimensional Display of the Functional Movements of an Arbitrary Mandible Point", Proceedings, vol. 602, Biostereometrics '85,Dec. 3–6, 1985, Cannes, France, SPIE, vol. 602, pp. 77–84.

Moran, Christopher J., M.D., et al., "Central Nervous System Lesions Biosied or Treated by CT–Guided Needle Placement," Neuroradiology, vol. 131, No. 3, Jun. 1979, pp. 681–686.

Mosges, Ralph, et al., "A New Imaging Method for Intraoperative Therapy Control in Skull–Base Surgery" (1988).

Mundinger, F., et al., "Treatment of Small Cerebral Gliomas with CT–Aided Stereotaxic Curietherapy," Neuroradiology, vol. 16, 1978, pp. 564–567.

Mundinger, F., et al., "Computer–Assisted Stereotactic Brain Operations by Means Including Computerized Axial Tomography," Applied Neurophysiology, vol. 41, No. 1–4, 1978, pp. 169–182.

Norman, David, M.D., et al., "Localization with the EMI Scanner," The American Journal of Roentgenology, Radium Therapy and Nuclear Medicine, vol. 125, No. 4, Dec. 1975, pp. 961–964.

O'Leary, M.D., Daniel H., et al. "Localization of vertex lesions seen on CT scan," J. Neurosurg, vol. 49, No. 1, Jul. 1978, pp. 71–74.

Obergfell, Klaus, et al., "Vision Sensing for Control of Long–Reach Flexible Manipulators," Research Paper, Georgia Institute of Technology, 6 pages.

Obergfell, Klaus, et al., "End–Point Position Measurements of Long–Reach Flexible Manipulators,"0 Research Paper, Georgia Institute of Technology, 6 pages.

Ohbuchi, R., et al., "Incremental Volume Reconstruction and Rendering for 3D Ultrasound Imaging," SPIE vol. 1808, Visualization in Biomedical Computing, pp. 312–323, Oct. 9, 1992.

Patil, Arun–Angelo, M.D., "Computed Tomography Plane of the Target Approach in Computed Tomographic Stereotaxis," Neurosurgery, vol. 15, No. 3, Sep. 1984, pp. 410–414.

Paul, et al., "Development of a Surgical Robot for Cementless Total Hip Arthroplasty," Clinical Orthopaedics, No. 285, Dec. 1992, pp. 57–66.

Pelizzari, C.A., et al., 3D Patient/Image Registration: Application to Radiation Treatment Planning, Medical Physics, vol. 18, No. 3, May/Jun. 1991, p. 612.

Pelizzari, C.A., et al., "Three Dimensional Correlation of PET, CT and MRI Images," The Journal of Nuclear Medicine, Abstract Book, 34th Annual Meeting, Toronto, Canada, 1987, vol. 28, No. 4, Poster Session No. 528, p. 682.

Pelizzari, Charles A., et al., "Accurate Three–Dimension Registration of CT, PET, and/or MR Images of the Brain," Journal of Computer Assisted Tomography, 13(1):20–26, Jan./Feb. 1989, pp. 20–26.

Pelizzari, C.A., et al., "Interactive 3D Patient–Image Registration," Information Processing in Medical Imaging, pp. 132–141, Jul. 1991.

Penn, Richard D. et al., "Stereotactic Surgery with Image Processing of Computerized Tomographic Scans," Neurosurgery, vol. 3, No. 2, pp. 157–163, Sep./Oct. 1978.

Perry, John H., Ph.D., et al., "Computed Tomography–guided Stereotactic Surgery: Conception and Development of a New Stereotactic Methodology," Neurosurgery, vol. 7, No. 4, Oct. 1980, pp. 376–381.

Picard, Claude, et al., "The First Human Stereotaxic Apparatus" J. Neurosurg., vol. 59, pp. 673–676, Oct. 1983.

Piskun, Walter S., Major, et al., "A Simplified Method of CT Assisted Localization and Biopsy of Intracranial Lesions," Surgical Neurology, vol. 11, Jun. 1979, pp. 413–417.

Pixsys Inc., "Offset Probe for Science Accessories' GP8–3ed digitizer," one page.

Pixsys Inc., "Real–Time Image–Guided Surgery and Planning, FlashPoint 3D Localizer," Investigational Device Brochure, 3 pages (unnumbered and undated).

Pixsys Inc., "PixSys: 3–D Digitizing Accessories," 6 unnumbered pages.

Pixsys Inc., "Design Aide" (Mar. 1989) 5 unnumbered pages.*

Pixsys Inc., "Alignment Procedure for the Pixsys Two–Emitter Offset Probe for the SAC GP–8–3D Sonic Digitizer," (undated) 3 unnumbered pages.*

Pixsys Inc. Company Information, Offering Memorandum, pp. 27–40.*

Pixsys Inc., "SACDAC User's Guide, Version 2e" (Mar. 1989) pp. 0–1 through 5–3.*

Reinhardt, H.F., "Sonic Stereometry in Microsurgical Procedures for Deep–Seated Brain Tumors and Vascular Malformations," Neurosurgery, vol. 32, No. 1, Jan. 1993, pp. 51–57.*

Reinhardt, H.F., et al., "Mikrochirugische Entfernung tifliegender Gefa.beta.mi.beta.bildungen mit Hilfe der Sonar–Stereometrie," Ultraschall in Med. 12 (1991) 80–84.*

Reinhardt, H.F., et al., "A Computer Assisted Device for the Intra Operate CT–Correlated Localization of Brain Tumors," (1988) Eur. Surg. Res. 20:52–58.*

Reinhardt, H.F., "Neuronavigation: A Ten–Year Review," Neurosurgery, vol. 23, pp. 329–341.*

Reinhardt, H.F., et al., "Interactive Sonar–Operated Device for Stereotactic and Open Surgery," Sterotac Funct Neurosurg, 1990; 54+55:393–397.*

Reinhardt, H.F., "Surgery of Brain Neoplasms Using 32–P Tumor Marker"Acta Neurochir 97:88–94, (1989).*

Reinhardt, H.F., et al., "CT–Guided 'Real Time' Stereotaxy," Acta Neurochirurgica Suppl. 46, 107–08, 1989.*

Roberts, M.D., David W., et al., "A Frameless Sterotaxic Integration of Computerized Tomographic Imaging and the Operating Microscope," J. Neurosurg., vol. 65, pp. 545–549, Oct. 1986.*

Rosenbaum, Arthur E., et al., "Computerized Tomography Guided Stereotaxis: A New Approach," Applied Neurophysiology, vol. 43,No. 3–5, Jun. 4–7, 1980, pp. 172–173.*

Sac Science Accessories Corporation, Technical Bulletin, "Model GP–8 Sonic Digitizer," "Mark II Sonic Digitizer (Model GP–7 Grafbar)," "3–Dimensional Sonic Digitizer (Model GP–8–3D)," U.S.A., 6 pages, not numbered, not dated.

Sautot, et al., "Computer Assisted Spine Surgery: a First Step Toward Clinical Application in Orthopaedics," IEEE, 1992.

Scarabin, J.M., et al., "Stereotaxic Exploration in 200 Supratentorial Brain Tumors," Neuroradiology, vol. 16, Jun. 4–10, 1978, pp. 591–593.

Schulz, Ph.D., Dean, President, PixSys, "Offset Probe for SAC GP8–3d digitizer," information flyer, not dated.

Sheldon, C. Hunter, M.D., et al., "Development of a computerized microstereotaxic method for localization and removal of minute CNS lesions under direct 3–D vision," J. Neurosurg, vol. 52, Jan. 1980, pp. 21–27.

Shiu, Y.C., et al., "Finding the Mounting Position of a Sensor by Solving a Homogeneous Transform Equation of Form AX×XB," IEEE, vol. 3, 1987, pp. 1666–1671.

Smith, Kurt R., et al., "Computer Methods for Improved Diagnostics Image Display Applied to Stereotactic Neurosurgery," Automedica, vol. 14, pp. 371–382, 1992.

Smith, Kurt R., et al., "Multimodality Image Analysis and Display Methods for Improved Tumor Localization in Stereotactic Neurosurgery," Annual Conference of the IEEE Engineering in Medicine and Biology Society, vol. 13, No. 1, p. 210, 1991.

Spencer, et al., "Unilateral Transplantation of Human Fetal Mesencephalic Tissue into the Caudate Nucleus of Patients with Parkinson'S Disease" The New England Journal of Medicine, vol. 327, No. 22, pp. 1541–1548, Nov. 26, 1992.

Stereotactic One Affordable PC Based Graphics for Stereotactic Surgery, 6 pages.

Stone, Harold S., "Moving Parts of an Image," McGraw–Hill Computer Science Series, (no date), pp. 254.

Valentino, D.J., et al., Three–Dimensional Visualization of Human Brain Structure–Function Relationships, The Journal of Nuclear Medicine, Oct. 1989, Posterboard 1136, vol. 30, No. 10, p. 1747.

Van Buren, J.M., et al., "A Multipurpose CT–Guidd Stereotactic Instrument of Simple Design," Applied Neurophysiology, Jan.–Aug. 1983, pp. 211–216.

Vandermeuler, D., et al., "A New Software Package for the Microcomputer Based BRW System," Integrated Stereoscopic Views of CT Data and Angiogram.

Wantanabe, et al., "Three Dimensional Digitizer (Neuronavigator): New Equipment for Computed Tomography–Guided Stereotaxic Surgery", 27 Sur. Neurol, 543–57 (1987) (with translation).

Wantanabe, Eiju, et al., "Neuronavigator," Igaku–no –Ayumi, vol. 137, No. 6, May 10, 1986, pp. 1–4.

Wolfe, William L., "The Infrared Handbook,", Office of Naval Research, Department of the Navy, Washington, D.C., 1978, pp. 22–63 through 22–77.

Wolff, Robert S., et al., "Visualization of Natural Phenomena," The Electric Library of Sciences, 1993, pp. 66–67.

Yeates, Andrew, M.D., et al., "Simplified and accurate CT–guided needle biopsy of central nervous system lesions," Journal of Neurosurgery, vol. 57, No. 3, Sep. 1982, pp. 390–393.

Adair, Taylor, et al.; "Computerized anatomy atlas of the human brain"; Computer and Information Science Department and the Cerebrovascular Research Center; University of Pennsylvania, Philadelphia, PA.; SPIE vol. 283, 3–D Machine Pereceptin; 1981; pp.116–121.

Adams, L. et al.; "Orientation Aid For Head and Neck Surgeons"; Innov. Tech. Biol. Med., vol. 13, No. 4, 1992; pp. 409–424.

Dhond, V.R. et al.; "Structure from Stereo—A Review"; IEEE Tranactions on System, Man and Cyberntics, vol. 19, No. 6, 1989, pp. 1489–1510.

Bajcsy, Ruzena et al.; "A Computerized System for the Elastic Matching of Deformed Radiographic Images to Idealized Atlas Images"; Journal of Computer Assisted Tomography; vol. 7, No. 4, Nov. 4, 1983; pp. 618–625.

Bajcsy, Ruzena et al.; "Evaluation of Registration of PET Images with CT Images"; Department of Computer and Information Science School of Engineering and Applied Science, University of Pennsylvania, Philadelphia, PA; Nov. 1988; pp. 1–14.

Bouazza–Marouf, K. et al.; "Robotic–assisted internal fixation of femoral fractures"; Proc. Institute Mechanical Engineers, vol. 209; 1995; pp. 51–58.

Brack, C. et al.; "Accurate X–ray–based Navigation in Computer–Assisted Orthopedic Surgery"; 1998 Elsevier Science B.V.; pp. 716–722.

Bucholz, Richard D. et al.; "The Correction of Stereotactic Inaccuracy Caused by Brain Shift Using an Intraoperative Ultrasound Device"; Surgical Navigation Technologies, Inc., Boulder, CO; pp. 459–466.

Bucholz, Richard D.et al,.; Image–Guided Surgical Techniques For Infections and Trauma of the Central Nervous System; Neurosurgery Clinics of North America; vol. 7, No. 2, Apr. 1996; pp. 187–200.

Christensen, Gary E. et al.; "3–D Brain mapping using a defomrable neuroanatomy"; Mechanical Engineering Department, Washington University, St. Louis, MO; 1994; pp. 609–618.

Collins, D. Louis, et al.; "An Automated 3D nonlienar image deformation procedure for Determination of Gross Morphometric Varability in Human Brain"; SPIE vol. 2359; Oct.4–7, 1994; pp. 180–190.

Davatzikos, Chris et al. "Brain Image Registration Based on Cortical Contour Mapping"; IEEE, 1994, pp. 1823–1826.

Davatzikos, Chris et al.; "Brain Image Registration Based on Curve Mapping"; IEEE, 1994, pp. 245–254, Dept. of ELectrical & Computer Engineering, John Hopkins University of Baltimore, MD.

Day, Richard et al.; "Three–Point Transformation for Integration of Multiple Coordinate Systems: Applications to Tumor, Functional, and Fractionated Radiosrugery Stereotactic Planning"; Proceedings of the XIth Meeting of the World Society for Stereotactic and Functional Neurosurgery, Ixtapa, Mexico, Oct. 11–15, 1993; p. 1.

Evans, A.C. et al.; "Image Registration Based on Discrete Anatomic Structures"; Chapter 5, pp. 63–80.

Evans, A.C. et al.; "Three–Dimensional Correlative Imaging: Applications in Human Brain Mapping"; Functional Neuroimaging; 1994; Chapter 14, pp. 145–161.

Evans, A.C. et al.; "Warping of a computerized 3–D atlas to match brain image volumes for quantitative neuroanatomical and functional analysis", SPIE vol. 1445; 1991; pp. 236–246.

Feldmar, Jacques et al.; "3D–2D projective registration of free–form curves and surfaces"; INRIA Sophia–Antipolism Dec. 1994; pp. 1–44.

Foley, Kevin T. et al.; "Image–guided Intraoperative Spinal Localization"; Intraoperative Neuroprotection, 1996; Chapter 19; Part Three, pp. 325–340.

Friston, K.J. et al.;"Spatial Registration and Normalization of Images"; Wiley–Liss, Inc.; 1996; pp. 165–189.

Golfinos, John G. et al.; "Clinical use of a frameless stereotactic arm: results of 325 cases"; Journal of Neurosurgery, vol. 83,No. 2; Aug. 1995; pp. 197–205.

Gramhow, Claus; "Registration of 2D and 3D Medical Images"Lyngby 1996; pp. 5–326.

Grimson, W. Eric L. et al.; "Virtual–reality technology is giving surgeons the equivalent of x–ray vision, helping them to remove tumors more effectively, to minimize surgical wounds and to avoid damaging critical tissues", Scientific America; Jun. 1999; pp. 63–69.

Gueziec, Andre P. et al.; "Registration of Computed Tomography Data to a Surgical Robot Using Fluoroscopy: A Feasbility Study"; Computer Science/Mathematics, Sep. 27, 1996; pp. 1–6.

Hamadeh, Ali et al.; "Anatomy–based Registration for Computer–integrated Surgery"; First International Conference CVR Med '95 Nice, France, Apr. 3–6, 1995; pp. 212–218.

Hamadeh, Ali et al.; "Automated 3–Dimensional Computed Tomographic and Fluoroscopic Image Regisration"; Wiley –Liss, Inc.; 1998, Computer Aided Surgery, vol. 3, pp. 11–19.

Hamaden, Ali et al.; "Kinematic Study of Lumbar Spine Using Functional Radiographies and 3D/2D Registration"; First Joint Conference Compuer Vision, Virtual Reality and Robotics in Medicine and Medical Robotics and Computer–Assisted Surgery, Grenoble, France, Mar. 19–22, 1997; pp. 109–118.

Hofstetter, R. et al.; "Fluoroscopy Based Surgical Navigation—Concept and Clinical Applications"; Computer Assisted Radiology and Surgery, 1997; pp. 956–960.

Horn, Berthold K.P.; "Closed–form solution of absolute orientation using unit quarternions"; 1987 Optical Society of America; pp. 629–642.

Joskowicz, Leo et al.; "Computer–Aided Image–Guided Bone Fracture Surgery: Concept and Implementation"; 1998 Elsevier Science B.V., Excerpta Medica International Congress Series 1165, pp. 710–715.

Kelly, Patrick; "The NeuroStation System for Image–Guided. Frameless Stereotaxy"; Neyrisyrgertm vol. 37, No. 1, Aug., 1995; pp. 348–359.

Kondziolka, Douglas et al.; "Guided Neurosurgery Using the ISG Viewing Wand"; Contemporary Neurosurgery, vol. 17, No. 8; 1995; pp. 1–6.

Kwoh, Yik San et al.; "A Robot with Improved Absolute Positioning Accuracy for CT Guided Stereotactic Brain Surgery"; IEEE; 1998; pp. 153–160.

Laitinent, Lauri V., "Noninvasive multipurpose stereoadapter"; Neurological Research, 1987; vol. 9, Jun. 1987; pp. 137–141.

Lavallee, S. et al.; "Computer–Assisted Spine Surgery: A Technique for Accurate Transpedicular Screw Fixation Using CT Data and a 3–D Optical Localizer"; 1995 Wiley –Liss, Inc.; vol. 1, No. 1; pp. 65–73.

Lemieuz, L. et al.; "A patient–to–computed–tomography image registration method based on digitally reconstructed radiographs"; Medical Physics, vol. 21, No. 11; Nov. 1994; pp. 1749–1760.

Levy, Michael L. et al.; Heads–up Intraoperative Endoscopic Imaging: A Prospective Evaluation of Techniques and Limitations; Neurosurgery, vol. 40, No. 3, Mar. 1997; pp. 526–532.

Maurer, Jr., Calvin R., et al.; "A Review of Medical Image Registration"; Chapter 3; pp. 17–44.

Mayberg, Marc R. et al.; "Neurosurgery Clinics of North America"; W.B. Saunders Company; vol. 7, No. 2; Apr. 1996; pp. xv–xvi.'

Nowinski, Wieslaw, et al.; "Talairach–Tournoux/Schaltenbrand–Wahren Based Eletronic Brain Atlas System"; Department of Radiology, Johns Hopkins University, Baltimore, MD; pp. 257–261.

Olivier, Andre et al.; "Frameless stereotaxy for surgery for epilepsies: preliminary experience"; Journal of Neurosurgery, vol. 81, No. 4, Oct. 1994; pp. 629–633.

Phillips, R. et al.; "Image guided orthopaedic surgery design and analysis"; Transactions of The Institute of Measurement and Control, vol. 17, No. 5, 1995; pp. 251–264.

Pollack, Ian F. et al.; "Frameless Stereotactic Guidance An Intraoperative Adjunct in the Transoral Approach for Ventral Cerviocmedullary Junction Decompression"; Spine, vol. 20, No. 2, 1995; pp. 216–220.

Saw, Cheng B.; "Coordinate transformations and calculation of the angular and depth parameters for a stereotactic system"; Medical Physics, vol. 14, No. 6; Nov./Dec. 1987; pp. 1042–1044.

Smith, Kurt R.; "The Neurostation—A Highly Accurate Minimally Invasive Solution to Frameless Stereotactic Neurosurgery"; Computerized Medical Imaging and Graphics, vol. 18, No. 4, 1994, pp. 247–236.

Takizawa, Takaaki; "Neurosurgical Navigation Using a Noninvasive Stereoadapter"; 1993 Elsevier Science Publishing Co., Inc., vol. 30, pp. 299–305.

Toga, Arthur E.; "Three–Dimensional Neuroimaging"; Raven Press New York 1990; Chapter 9; pp. 194–209.

Undrill; PE et al.; "Integrated presentation of 3D data derived from multi–sensor imagery and anatomical atlases using a parallel processing system"; SPIE, 1991, vol. 1653, pp. 2–16.

Weese, Jurgen; et al.; "An Approach to 2D/3D registration of a Vertebra in 2D X–ray Fluoroscopies with 3D CT Images"; CVRMed–MRCAS '97; First Joint Conference Computer Vision, Virtual Reality and Robotics in Medicine and Medical Robotics and Computer–Assisted Surgery; Grenoble, France Mar. 19–22, 1997; pp. 119–128.

Woods, Roger P. et al.; "MRI–PET Registration with Automated Algorithm"; Journal of Computer Assisted Tomography, vol. 17, No. 4; Jul./Aug. 1993; pp. 536–545.

Colins, D. Louis, et al.; "Automatic 3D Intersubject Registration of MR Volumetric Data in Standardized Talairach Space", Journal of Computer Assisted Tomography, vol. 18, No. 2, pp. 192–205, Mar./Arp. 1994, Raven Press, Ltd., New York.

* cited by examiner

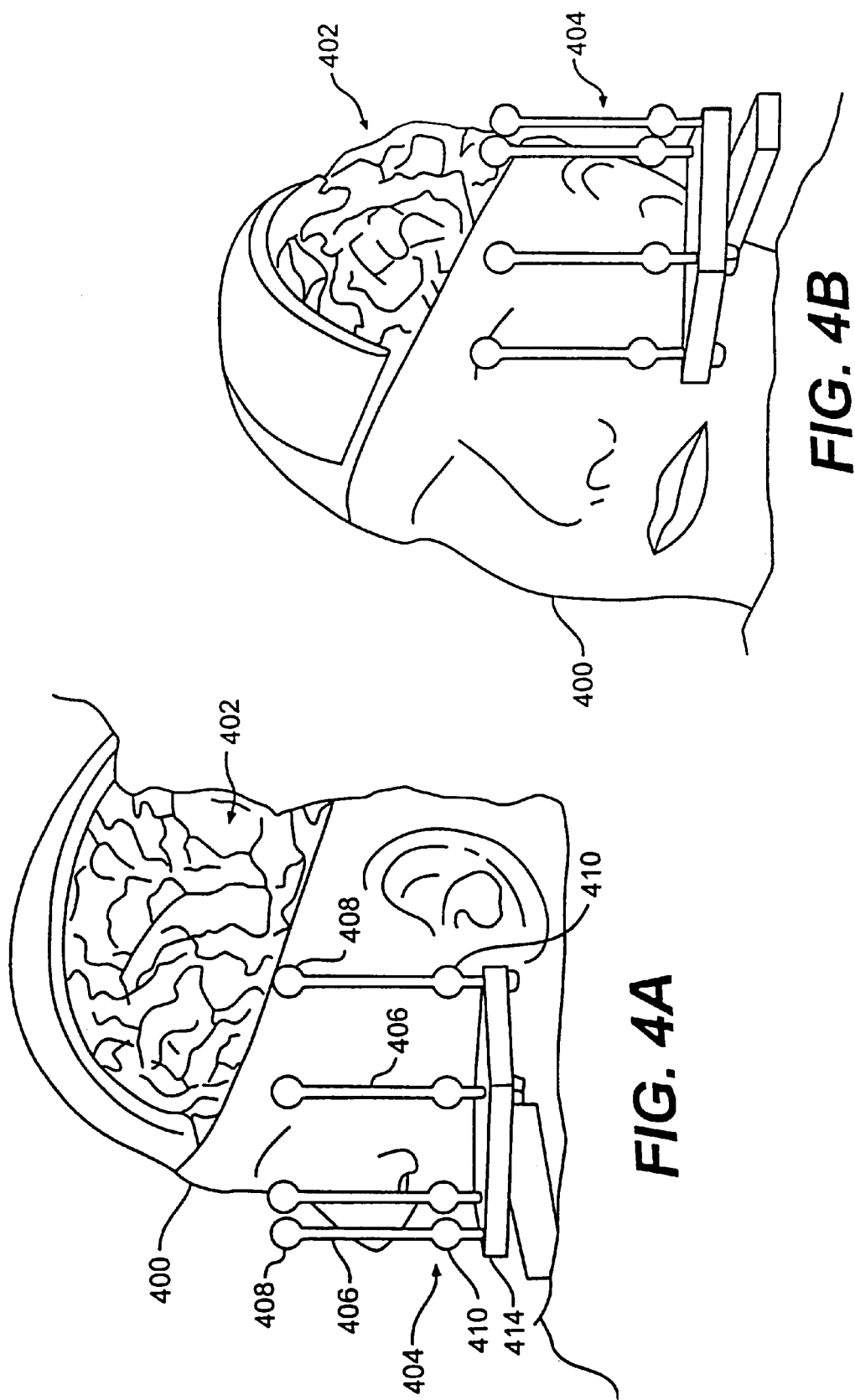

APPARATUS AND METHOD FOR PHOTOGRAMMETRIC SURGICAL LOCALIZATION

RELATED APPLICATIONS

This is a divisional of application Ser. No. 09/635,594, filed Aug. 9, 2000 now abandoned, which is a continuation of application Ser. No. 09/513,337, filed on Feb. 25, 2000 now U.S. Pat. No. 6,146,390, which is a continuation of application Ser. No. 09/173,138 filed Oct. 15, 1998 now U.S. Pat. No. 6,165,181, which is a continuation of application Ser. No. 08/801,662 filed on Feb. 18, 1997, now U.S. Pat. No. 5,836,954, which is a continuation of application Ser. No. 08/145,777, filed on Oct. 29, 1993, now U.S. Pat. No. 5,603,318, which is a continuation-in-part of application Ser. No. 07/871,382, filed on Apr. 21, 1992, now U.S. Pat. No. 5,389,101, all of which are incorporated herein by reference.

BACKGROUND OF THE INVENTION

1. Field

The application is related to techniques for mapping internal structures in the body of an animal or human, and more particularly to such technique for localizing a medical instrument with respect to anatomical features or the like during surgical or other medical procedures.

2. State of the Art

Various scanning apparatus and methods are known for imaging and mapping body structures, which provide target location data for surgical and other medical procedures. One group of methods, including still photography, videography, radiological x-rays, and angiography, typically produces only a two-dimensional projection of a three-dimensional object. For purposes of this application, this first group will be termed "two-dimensional" or "2D" imaging.

A second group of methods, of which computerized tomographic (CT) scanning, positron emission tomography (PET) scans, and magnetic resonance (MRI) imaging are exemplary, provides three-dimensional (abbrev. "3D" herein) information about internal structures (i.e., structures not visible from the exterior of the patient). The three-dimensional information about the internal volume is reconstructed from multiple scans of a known thickness (generally about a millimeter) made along parallel planes displaced from each other by a known distance, usually of the order of millimeters. An example of such a reconstructed volume image is depicted in FIG. 1A, including the contours of a selected anatomical feature within the brain. In this application, methods of this second group will be referred to as "volume" scanning or imaging.

In performing resection or other surgical manipulations, it is highly desirable to correlate the location of instruments, patient anatomical features, or other elements or structures placed in the surgical field, and generally as seen by the surgeon, with the location of internal targets or features as visualized by one of the volume scanning techniques. Such a correlation process is often termed "localization".

A commercially available device for localization in neurosurgery is the Brown-Roberts-Wells (abbrev. BRW) localizer (U.S. Pat. Nos. 4,341,220, and 4,608,977). The BRW system includes a large ring-like structure which surrounds the patient's head and is fixed in place. The ring establishes a 3D coordinate system with respect to the patient's head. A separate calibration unit having an array of rod elements is fixed to the ring to surround the head during the production of volume scan and/or 2D images. The rod elements have known coordinates in the 3D coordinate system established by the ring, and produce spots in the volume scans. Other features in the volume scans can then be assigned coordinates in the 3D coordinate system established by the ring, by correlation with the known coordinates of the rod elements producing the spots.

After the images are made, the calibration unit is detached from the ring, and a guidance arc calibrated to the 3D coordinate system of the ring is attached in its place. The guidance arc provides coordinate reference information which may be uses to guide a medical instrument. The medical instrument is usually attached to the guidance arc.

The BRW system has several disadvantages. The ring is cumbersome and uncomfortable for the patient, but it must be affixed in place when the volume and/or 2D scans are made, and kept there until the medical procedure is complete. It is possible to remove the ring after the scans are made, but precise repositioning is critical to avoid error in localization. Accurate repositioning is difficult, so present practice generally is to keep the ring in place until after the surgery. When not attached to the guidance arc, the position of a medical instrument in terms of the 3D coordinate system of the ring, and therefore in respect to the features identifiable in the volume or 2D scan, is not accurately known.

U.S. Pat. No. 4,618,978 to Cosman discloses a localizer device for use with a BRW-type system, including an open box composed of connected rods, which surrounds the patient's head and constitutes a calibration unit.

Alternatively, cranial implants of radio-opaque or MRI-opaque materials can be made. Generally, a minimum of three implants are required for establishing a three-dimensional space in volume scans. At present this method is considered very undesirable, in part because of the risk of infection or other complications of the implants.

Accordingly, a need remains for rapid, reliable, and inexpensive means for localizing a medical instrument relative to points of interest including both visible anatomical features and internal features imaged by volume and/or 2D methods. A need further remains for such means which does not require the physical attachment of a reference unit such as the BRW ring to the patient. Highly desirably, such means would be useful to track the position of a medical instrument in real time, and without requiring that the instrument be physically attached to a reference guide.

Other Terms and Definitions

A coordinate system may be thought of as a way to assign a unique set of numerical identifiers to each point or object in a selected space. The Cartesian coordinate system is one of the best known and will be used in this paragraph by way of example. In the Cartesian coordinate system, three directions x, y, z are specified, each corresponding to one of the three dimensions of what is commonly termed 3D (three-dimensional) space (FIG. 1B). In the Cartesian system, any point can be identified by a set of three values x, y, z. The x, y and z directions can be said to establish a "three-dimensional framework" or "coordinate framework" in space. A selected point "A" can be described in terms of its values $x_a$, $y_a$, $z_a$; these values specify only the location of point A. A different point B will have a different set of values $x_b$, $y_b$, $z_b$. Such a set of values x,y,z for any selected point is referred to herein as the "coordinates" or "locational coordinates" of that point. When the position of a feature larger than a single point is being described, these terms are also understood to refer to a plurality of sets of x,y,z values. Other types of coordinate systems are known, for example spherical coordinate systems, and the terms "coordinates" and "locational coordinates" should further be understood to apply to any set of values required to uniquely specify a point in space in a given coordinate system.

The term "fiducial" is used herein as generally understood in engineering or surveying, to describe a point or marking, or a line, which is sufficiently precisely defined to serve as a standard or basis reference for other measurements.

SUMMARY OF THE INVENTION

The invention comprises apparatus and a method for defining the location of a medical instrument relative to elements in a medical workspace including a patient's body region, especially (but not limited to) elements seen by the surgeon. The apparatus develops a calibrated 3 dimensional framework of the workspace from a pair of 2D images made from different fixed locations, and aligns the workspace framework with a 3D scan framework defined by a volume scan. A pair of video cameras is the present preferred imaging means for obtaining the 2D image pairs. The apparatus is then operable to locate and track the position of a medical instrument during a medical procedure, with respect to features observable in either the workspace images or in the volume scan. A pictural display of such location and tracking information is provided to aid a medical practitioner performing the procedure.

In a further embodiment, the computing means is operable to automatically recognize and track the position of selected medical or surgical instruments during a procedure, from the workspace images.

The apparatus may be described as follows. Workspace imaging means are provided and positioned for producing a plurality of pairs of 2-dimensional images of a medical workspace. Each image pair comprises two such images made in effect simultaneously along respective different sightlines which intersect at an angle. Digitizing means are operably disposed for digitizing each image to produce corresponding sets of digital output signals, one set for each image.

Calibration means are removably positionable in the workspace for calibrating the workspace in terms of a three-dimensional coordinate framework. The 3D workspace framework is derived by computation from the two 2D projections of an image pair made with the calibration means positioned in the workspace. The calibration means comprises a set of at least six fiducial points connected by a frame means consisting of a frame constructed to hold the fiducial points in fixed spatial relation to each other. Although a calibration means with a set of at least six fiducial points is preferred, it is understood that the calibration means only requires a sufficient number of fiducial points to derive the 3D workspace framework. The frame need not include any means for attaching the fiducial points to a patient. The set of fiducial points has known spatial parameters which define an arbitrary Cartesian 3-dimensional coordinate system. These spatial parameters include 3D location coordinates of each of the fiducial points. Optionally but desirably, at least some of the actual distances between fiducial points should be known, to calibrate the workspace in terms of a suitable distance unit such as millimeters.

A computing means is connected to receive the digital output signals reflective of the images. The computing means also has data input means for receiving scan data from a volume scan of the patient's body region. The scan data define a scan 3D coordinate framework and internal anatomical structures therein. The computing means is further constructed or programmed to perform the following steps: 1) establish a workspace coordinate framework in three dimensions from an image pair made with said fiducial structure positioned within the workspace; 2) determine the locational coordinates in the workspace framework of any selected point which can be identified from both images of said pair; 3) correlate the scan locational coordinates for each of three or more selected landmarks observable in the scan with the workspace locational coordinates of the same landmarks as derived from a video image pair; 4) use the correlation of the workspace coordinates and the scan coordinates of the landmarks, to derive a transformation algorithm for mapping selected other features from either the scan framework to the workspace framework, or the converse; and 5) provide display signals encoding a display reflective of one or both of the workspace images and/or a volume scan, as selected by a user. Display means are provided for displaying the images encoded by the display signals.

Optionally but highly desirably, the computing means has computer graphics capability for producing graphic icons overlaid upon the displayed images. Such icons include a cursor which the user employs to select features in the displayed images for computation of their coordinates or other operations.

A method of surgical guidance may be described as follows. First, a fiducial structure having six or more fiducial points defining two distinct, non-orthogonal planes is positioned in a medical workspace. Workspace imaging means are disposed for making pairs of two-dimensional images of the workspace in which the two member images are made along different but intersecting sightlines. A calibration image pair comprising images of the workspace with the fiducial structure is made. The fiducial structure is removed from the workspace.

A projection algorithm is applied to reconstruct a workspace 3D coordinate framework from the calibration image pair. At least one additional 3D scan framework is obtained from a corresponding volume scan of the patient's body region. At least three landmarks identifiable in both the volume scan and the workspace image pair are selected, and the coordinates for the three landmarks are determined in both the workspace framework and the scan framework. From these determined coordinates, a process is developed for aligning the scan framework with the workspace framework, and transformation algorithms for converting coordinates from one of the frameworks to the other are computed.

A target of interest in the volume scan is identified, and its scan coordinates are determined and converted to workspace coordinates. A feature of interest in the workspace, such as a fiducial mark on a scalpel, is identified. The workspace coordinates of the fiducial mark and of the scalpel tip (whose distance from the fiducial mark is known), plus a vector describing the direction of the scalpel, are determined. Optionally but highly desirably, both the target and the scalpel including the scalpel tip position are displayed in an image of the workspace. The path of the scalpel tip is extrapolated along the vector for a distance sufficient to determine whether the tip will reach the target on this path. If not, the direction of the scalpel is adjusted and the process of localizing the tip and extrapolating its path is repeated until the extrapolated path is deemed adequate by a user, and/or until the medical procedure is complete.

The invention also includes a fiducial structure for establishing a three-dimensional coordinate framework for a photographic image pair, comprising a sufficient number of fiducial indicators arranged to a three-dimensional coordinate system and frame means for supporting and connecting the fiducial indicators, wherein the frame means consists of a frame constructed to hold the fiducial indicators in fixed relation to each other.

BRIEF DESCRIPTION OF THE DRAWINGS

In the figures, which illustrate what is presently regarded as the best mode for carrying out the invention, like reference numbers indicate like elements of the apparatus:

FIG. 4 depicts a pair of images made from different positions of a surgical workspace including a patient's head, with the fiducial structure of the invention positioned for calibrating the workspace;

DETAILED DESCRIPTION OF THE ILLUSTRATED EMBODIMENT

Figure 1A:
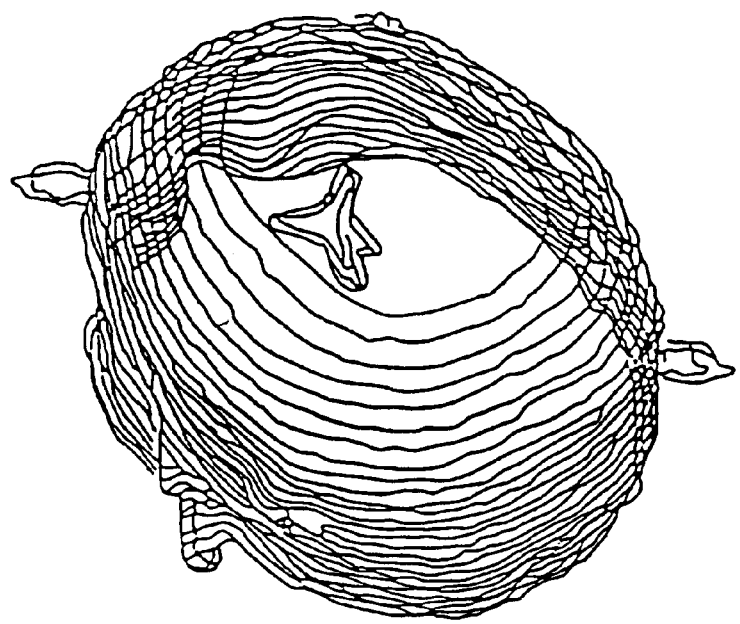
FIG. 1A is a cartoon of a volume scan of a patient's head.
Figure 1B:
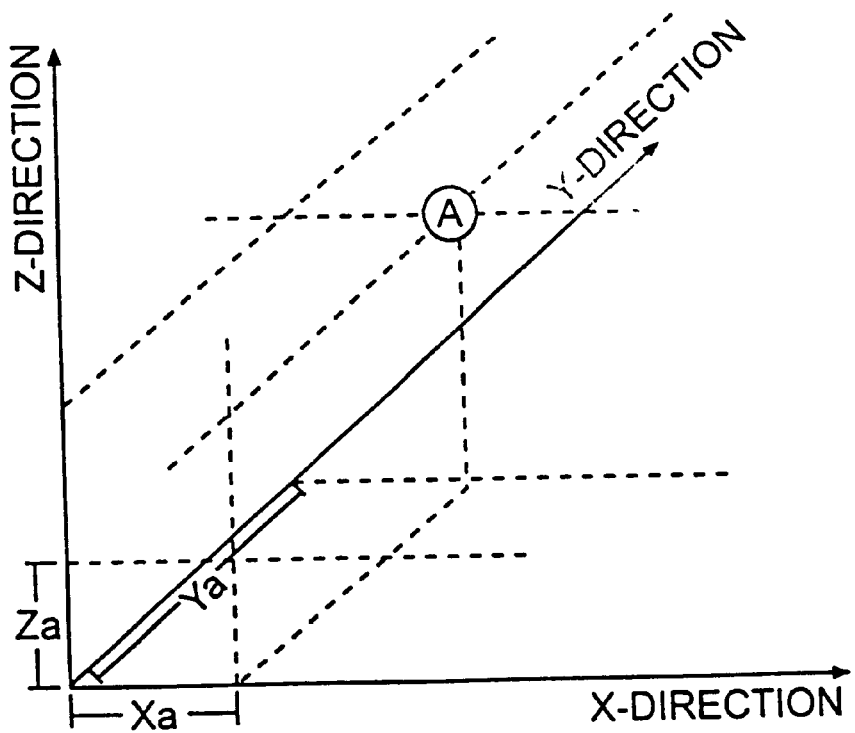
FIG. 1B depicts a 3-dimensional coordinate system.
Figure 2:
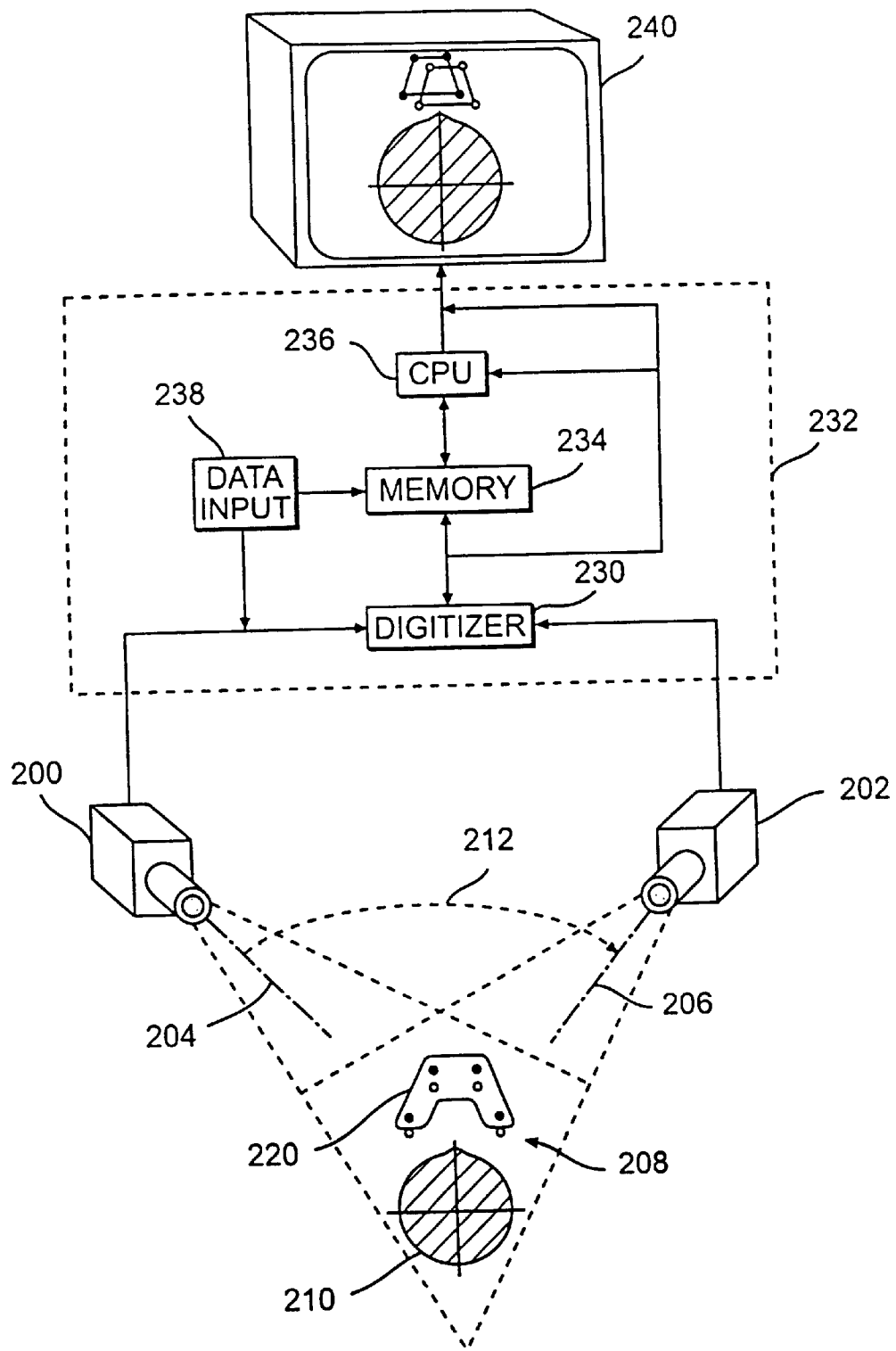
FIG. 2 is a block diagram depicting the basic elements of a video localization system of the invention.

FIG. 2 is a block diagram depicting the basic elements of a working embodiment of a video localization system of the invention. A pair of video cameras 200, 202 are positioned for making a pair of images along respective sightlines 204, 206, of a medical workspace 208 which includes a patient's body region here shown to be the patient's head 210. Cameras 200, 202 are arranged to have an angle 212 between sightlines 204, 206, such that both cameras image the workspace 208. Workspace 208 is effectively defined by the overlapping fields of view of the respective images made by cameras 200, 202. Angle 212 is preferably between about 30° and 150°. However, any angle greater than zero degrees and not equal to 180° can be used.

Alternatively, cameras 200, 202 may be replaced by a single camera which is moved back and forth between first and second positions to take images along respective sightlines 204, 206. In the latter case, it is important that the camera be precisely positioned in the first and second positions when making the respective images of an image pair. Positioning means may be provided for establishing fixed attachment points for attachment of a camera, to facilitate such repositioning. Whether one camera or two cameras are used, what is significant is that the system takes pairs of images of workspace 208, each member of an image pair made along different sightlines intersecting in workspace 208.

A fiducial structure 220 (described in greater detail with reference to FIG. 3) is shown positioned in the workspace 208 proximal to the head 210. During use, fiducial structure 220 can be held in position by any suitable support means (not shown). One suitable support means would be a bar with a clamp arm attached to a ring stand or the like. Notably, fiducial structure 220 is neither affixed to, nor in contact with, the patient's head 210. Fiducial structure 220 may be removed from workspace 208 when it is not required.

Cameras 200, 202 are communicatively connected to image digitizing means 230, which produces two sets of digitized image signals, each representative of a respective image detected by one of the two cameras. Digitizing means 230 is in turn connected to send the digitized image signals to computing means 232.

Computing means 232 receives the digitized image signals from digitizing means 230 and is operable in response to compute display signals representative of the digitized video image(s) of workspace 208 as seen by one or both of cameras 200, 202. Computing means 232 comprises at least a central processing unit, memory means which includes both volatile and nonvolatile memory components, data input means, an image processing/computer graphics subunit, and output means for outputting display signals. The foregoing components of computing means 232 are functionally interconnected generally as known in the art of computing. In a further embodiment, computing means 232 is operable to combine images of the workspace made from each of the two different positions to produce a single stereo image.

Computing means 232 supplies the display signals to a display unit 240 which may be a video display, a CRT monitor, or the like. Display unit 240 converts the display signals to a video image of the workspace 208 as seen by either or both of cameras 200, 202. Display unit 240 is positioned for ready viewing by medical personnel performing procedures in the workspace. Preferably, display unit 240 is constructed to provide sufficient resolution to adequately distinguish significant components in images of the workspace 208. In FIG. 2, display unit 240 is depicted as having a single viewing screen showing the image as seen by camera 200. This embodiment is provided with a single screen for displaying visual depictions of the available scans and images. These may include the image made by camera 200, the image made by camera 202, scan images derived from volume scanning methods, X-ray images made by X-rays and including angiograms, etc., as selected by a user operating computing means 232. The user may switch the display from one to another of the various visual depictions, as desired. Also, one or more features of a first selected depiction, or the entire first selected depiction, can be overlaid on a second selected view.

Alternatively, display unit 240 may contain a plurality of viewing screens arranged for simultaneously displaying in separate screens, the selected depictions.

Computing means 232 also provides graphic display signals to the display unit 240, to produce graphic icons overlaid upon the selected displayed image. The graphic icons should include a cursor which can be positioned by the user at a feature of interest in the displayed image.

Computing means 232 is further constructed, or alternatively programmed, to compute a workspace coordinate framework which defines workspace 208 in terms of three-dimensional Cartesian coordinates in useful distance units, for example millimeters. The workspace coordinate framework is computed from the two digitized 2-dimensional images of the fiducial structure 220 provided respectively by cameras 200, 202, plus the known location parameters of fiducial points on fiducial structure 220 (described in more detail in reference to FIG. 3). In the working embodiment, computing means 232 performs these computations according to a well-known projection algorithm, originally developed by Bopp and Krauss (Bopp, H., Krauss, H., An orientation and calibration method for non-topographic applications, *Photogrammetric Engineering and Remote Sensing*, Vol. 44, Nr. Sep. 9, 1978, pp. 1191–1196).

The memory means of computing means 232 is constructed or programmed to contain the known location parameters of fiducial structure 220, which are required for performance of the computations producing the workspace coordinate framework from the two 2D images. In the working embodiment, these known location parameters include three-dimensional Cartesian coordinates for each of the fiducial points and the actual distances between some of the fiducial points as measured from fiducial structure 220. The latter distances are not required for establishing the workspace framework, but are used to calibrate the framework in terms of useful real distance units.

Once the workspace coordinate framework has been computed, computing means 232 is further operable to compute the 3D location coordinates within the workspace framework of any feature of interest whose position may be observed by means of the images made with both of cameras 200, 202. Such workspace location coordinates will be accurate provided the two images are made from substantially the same positions relative to workspace 208 as during the establishment of the three-dimensional framework with the fiducial structure.

Features which can be observed by means of the images made by cameras 200, 202 include both features actually seen in both images, and features which are not within the field of view of one or both images but whose position can be indicated by use of a pointer with at least two fiducial marks, where the distance between at least one of the fiducial marks and the tip of the pointer is known. Two fiducial marks are needed to establish the direction with respect to the workspace coordinate framework, of a vector representing the linear direction of the pointer. Alternatively, any other marker(s) useful to compute the vector direction may be employed.

Examples of features of interest include externally-placed portions of scan markers used for volume and/or 2D scans, anatomical features on or within the patient including skull surface contours, marks on the patient's skin, medical instruments and devices, etc.

Computing means 232 further has data input means 238 for receiving data representing one or more scans produced by volume imaging methods (PET, MRI, CT) and/or by 2D imaging methods (X-rays, angiograms) etc. In an alternate embodiment, computing means digitizes the CT and/or MRI volume scans and integrates the digitized volume data to establish the volume scan 3D coordinate system.

Once the workspace coordinate framework and any volume scan coordinate framework(s) have been established, computing means 232 is further operable to apply standard mathematical methods to align the scan coordinate framework(s) with the workspace framework. Knowledge of the coordinates in both the scan framework and the workspace framework of each of three selected landmarks is required and is sufficient for the alignment. Such landmarks may be anatomical features, scan markers which produce distinctive spots in the scan, or any other feature which can be unequivocally identified in both the images made by the imaging means and in the scan.

Using information derived from the mathematical operations used to align the volume scan framework with the workspace framework, computing means 232 is further operable to derive transformation functions for converting scan location coordinates describing the position of a selected point in terms of the scan framework, to workspace location coordinates which describe the position of the same selected point in terms, of the workspace framework. A term used in the art for this conversion process, which will also be used for purposes of this application, is "mapping" of coordinates from one framework to another.

Computing means 232 may also perform the converse operation, e.g. to map coordinates of a selected point from the workspace framework to the volume scan framework.

In a further embodiment, the system includes means for attaching at least two fiducial marks to instrument(s) to be used in the workspace. Alternatively, a set of instruments having at least two fiducial marks may be provided as part of the system. These fiducial marks permit tracking of the position of an operative portion of the instrument and extrapolation of its path. These operations will be described in greater detail hereinafter. In still another embodiment, features normally present on a medical instrument may be used as the fiducial marks, provided the distance between at least one of such marks and the operative portion is measured and provided to computing means 232.

In the working embodiment depicted in FIG. 2, which is a currently preferred embodiment, computing means 232, digitizing means 230, and display unit 240 take the form of a computer workstation of the type commercially available, having standard image processing capability and a high-resolution monitor. In this embodiment, the digitizing of all of the images made by the workspace imaging means, digitizing of the volume scan data, establishment of the workspace coordinate framework, and other functions described herein for computing means 232, may be accomplished in large part or entirely by appropriate software means stored in the memory portion of the computer workstation.

When an image of the fiducial structure is taken by an optical imaging means such as a video camera or X-ray machine, a two dimensional projection of the structure is produced. If two such images (an image pair) are taken at different angles, for example by cameras 200, 202 in FIG. 2, the two 2D projections can be used to reconstruct the three dimensional coordinate system of the fiducial structure, using any suitable-photogrammetric projection algorithm.

In the working embodiment, the photogrammetic projection computations are based upon a well-known projection algorithm (Bopp, H., Krauss, H., An orientation and calibration method for non-topographic applications, *Photogrammetric Engineering and Remote Sensing,* Vol. 44, Nr. Sep. 9, 1978, pp. 1191–1196), which has previously been applied to derive from X-ray images a coordinate system referenced to a BRW-type ring localizer (Siddon, R., and Barth, N., "Stereotaxic localization of intracranial targets", *Int. J. Radiat. Oncol. Biol. Phys.* 13:1241–1246, 1987; P. Suetens et al., "A global 3D image of the blood vessels, tumor, and simulated electrode", *Acta Neurochir.* 33:225–232, 1984; D. Vandermeulen et al., "A new software package for the microcomputer based BRW stereotactic system: integrated stereoscopic views of CT data and angiograms", *SPIE* 593:106–114, 1985).

It should be noted that while the fiducial structure, the method and the computations are described primarily with reference to a Cartesian coordinate system, other types of 3D coordinate systems may be used instead. Such alternate coordinate systems include spherical coordinates, cylindrical coordinates, and others. Any of these alternate coordinate systems could be applied in place of the Cartesian system, with appropriate changes in the projection computations, to accomplish essentially the same goals in substantially the same way. The fiducial structure would be used in essentially the same way. However, depending on the type of coordinate system employed, other arrangements of the fiducial points of the fiducial structure may be desirable. For example, with a spherical coordinate system, fiducial points presented as a spheroidal array instead of a box-like array, might be more convenient for the computations. Also, the minimum or sufficient number of fiducial points required for the projection computation may differ for different projection algorithms. The number of required fiducial points would be evident from the projection algorithm selected.

To utilize the projection technique of Bopp and Krauss in a Cartesian system, the fiducial structure should meet the following criteria. First, the fiducial structure must have at least six fiducial points arranged to define two distinct planes. Second, the actual coordinates of each of the individual fiducial points must be known and must be fixed relative to the other fiducial points. Optionally but highly desirably, the linear distance between at least one pair of fiducial points should be measured from the fiducial structure and stored in the computing means, to provide a distance reference to calibrate the workspace in terms of real distance units. However, other methods of calibrating the workspace in distance units could be used.

Figure 3A:
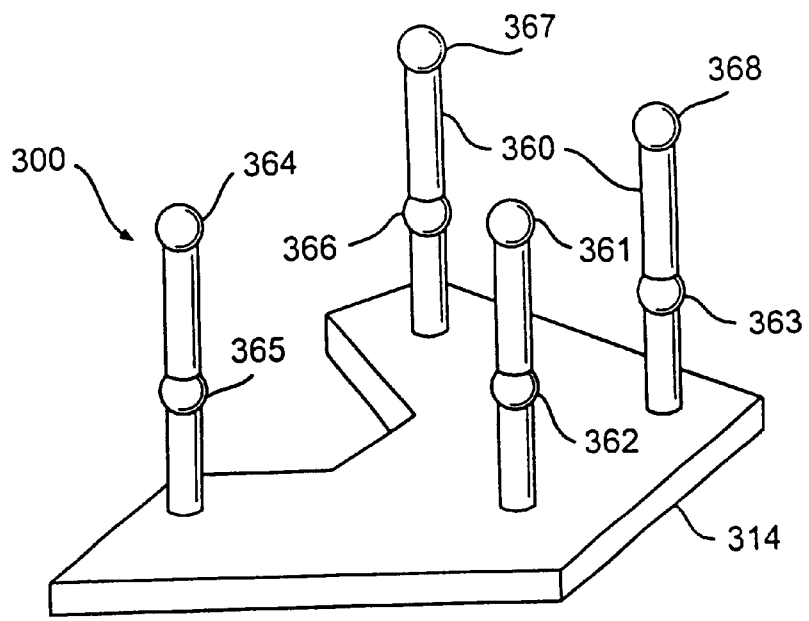
FIG. 3 depicts an embodiment of the fiducial structure in greater detail.
Figure 3B:
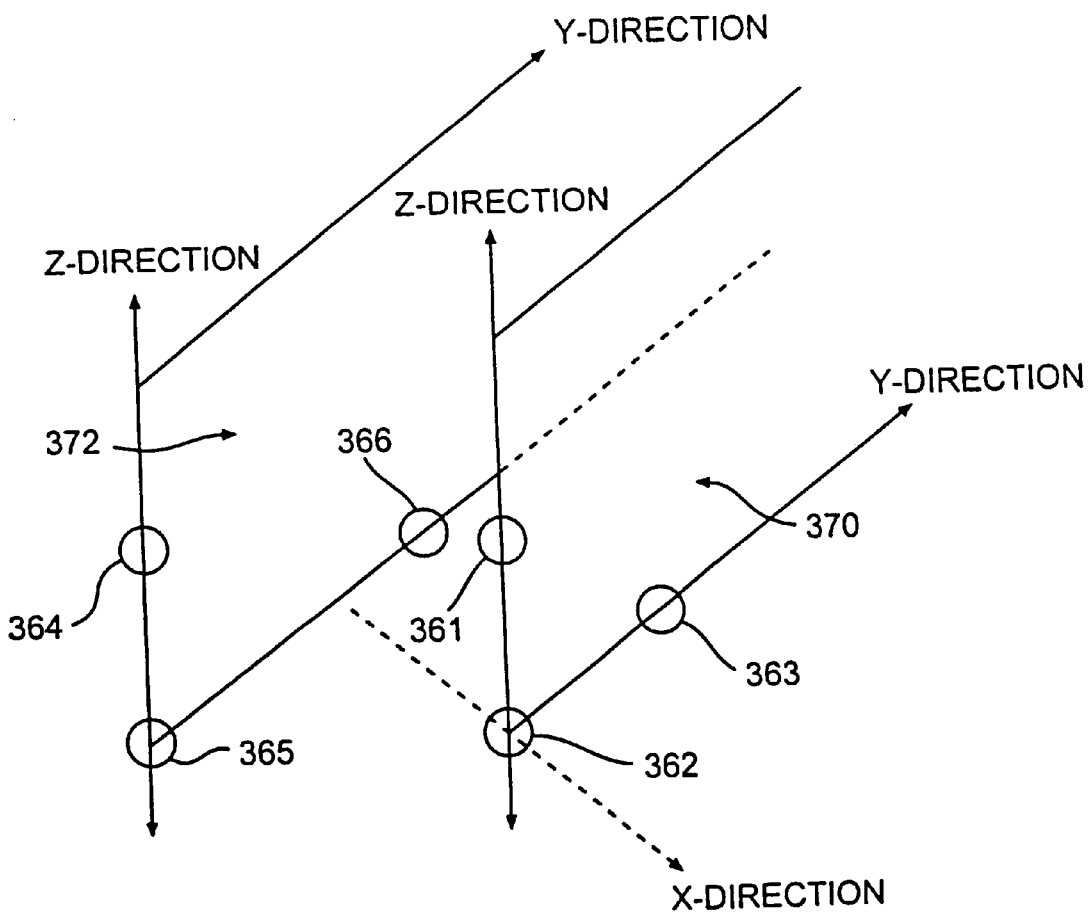

In the embodiment of FIG. 3, fiducial structure 300 has four rods 360 each having respective upper and lower ends 310, 320. Eight fiducial points 361, 362, 363, 364, 365, 366, 367, 368 are formed as balls on rods 360. Each of rods 360 is fixed at its lower end 310 to a plate 314. The attachment of rods 360 to plate 314 may be either detachable or permanent.

In the illustrated embodiment, planes 370, 372 are shown as being parallel; this is not required, but the planes cannot be orthogonal to each other. It is believed that the greatest accuracy in the mathematical calculations will be achieved if the planes are parallel or near to parallel.

An arrangement of the fiducial points in parallel planes and along lines perpendicular to those planes to form an open square or rectangular box provides a simple configuration for defining the coordinates of the fiducial points within the coordinate framework of the calibration unit. However, the trapezoidal arrangement depicted in FIG. 3 is currently preferred. In use, the trapezoidal fiducial structure of FIG. 3 is placed with fiducial points 364, 365, 366 rearward and closer to the patient, and fiducial points 361, 362, 363 forward and nearer to the workspace imaging means. The arrangement having the "rearward" fiducial points of the fiducial structure spread farther apart than the forward points is believed to be easier to position such that none of the fiducial points is obscured or blocked in either of the images made by cameras 200, 202. In a further preferred embodiment, the "rearward" fiducial points are constructed to be distinguishable from the "forward" fiducial points. This may be accomplished by making them of differing shapes (say boxes vs. balls), differing colors, etc.

The connecting elements constituted by rods 360 of FIG. 3 need not be arranged as a trapezoid, a rectangle or any other regular figure. Nor is it required that the fiducial points in the first plane be positioned directly above the points in the second plane. It will also be apparent that the fiducial structure need not have a plate such as plate 314, rods such as rods 360, or fiducial points shaped as balls as in FIG. 3. All that is required is a minimum of six fiducial points arranged to satisfy the conditions described in the preceding paragraphs, and means for holding the fiducial points in fixed relation to each other. A rather different construction might for example be a clear plastic box-like structure with fiducial elements, either brightly visible marks or shapes such as balls, at appropriate corners. The fiducial identifiers need not be balls as shown in FIG. 3, but could be other shapes, including pyramids or boxes; markings on rods such as rods 360; vertices at the interconnections of rod-like elements, etc.

Optionally but desirably, as in the embodiment of FIG. 3, there are two additional fiducial points 367, 368, beyond the six required for the computations. The "extra" fiducial points may be used to verify that the computation of locational coordinates from the camera images is correct.

FIGS. 4A and 4B depict one embodiment of a fiducial structure as it would be seen in video and/or CRT displays of the respective images as seen by cameras 200, 202, of a workspace including a patient's head. The patient's head 400 has an exposed portion of the brain 402 which serves as the point of entry for a surgical procedure, and a fiducial structure 404 positioned adjacent thereto.

In a still further embodiment, a grid representing the workspace coordinate framework may be projected onto the workspace by means of a light projector analogous to a common slide projector, but using more concentrated light. Still another embodiment includes a spot projector like a laser spot, which projects a bright or colored spot onto the surface of the patient, the spot being detectable in image pairs made by the camera(s), and accordingly localizable by the same means as any other selected feature in the workspace. This spot projector can be aimed by a user to select a spot whose workspace coordinates it is desired to determine, or automatically by the computing means to indicate the coordinate location of a feature selected from another scan such as a volume scan.

The apparatus so designed is also functional to convert from a 3D coordinate framework established from two video 2D images, to a second 3D coordinate framework established from a similar pair of X-ray 2D images made with a calibration unit that has radio-opaque fiducial points. These X-ray images could be standard-type radiological X-rays, or angiograms. This X-ray coordinate framework can further be aligned with a volume scan framework in the same manner as for the video framework, and location coordinates of features in the X-ray images transformed to video coordinates or volume scan coordinates, as desired.

A sequence of steps of a method of localizing and guiding surgical instruments is described as follows, referring as needed to FIG. 2. The first step is to position cameras 200, 202 for viewing a medical workspace 208. The angle 212 between the sightlines 204, 206 is preferably from about 30 degrees to about 150 degrees.

Next, the fiducial structure is positioned within the workspace so as to have at least six fiducial points visible to both cameras. A pair of images is made in effect simultaneously, of the workspace with the fiducial structure therein, to produce a calibration image pair. The images from the respective cameras are digitized and 2 dimensional coordinates for each of the fiducial points in the 2D images made by each of cameras 200, 202 are determined. A projection algorithm, which in a working embodiment of the method is the Bopp-Krauss projection algorithm previously referenced herein, is then used to mathematically reconstruct a workspace 3D coordinate framework from the 2D coordinates from both images of the calibration image pair, plus the known location parameters of the fiducial points in the fiducial structure. The projection algorithm is optimized using a least-squares approach. All of the foregoing computations, and those described later, may desirably be performed by operating a computer workstation configured similarly to computing means 232.

Generally, it is preferred to make the calibration workspace image pair with the fiducial structure and the patient in the workspace, because it is easier to ensure that the desired body region of the patient is adequately centered within the workspace defined by the edges of the camera views. However, it is not required that the patient be in the workspace when the calibration image pair is made.

The fiducial structure 220 may be removed from the medical workspace 208 at any time after the calibration image pair has been made, so long as all subsequent image pairs are made from the same two locations.

Scan data from one or more volume scans in a corresponding scan 3D coordinate framework are then provided to the computer. These scan coordinates may be previously stored in a memory unit within, or operably associated with, the computer, or may be supplied at this time through an external data input. The workspace coordinates and scan coordinates of at least three points which can be identified in both the workspace 3D framework and in the scan 3D framework are obtained and are used to make the alignment computations. These three points may be portions of the scan markers used in the internal scans which are also visible to both cameras in the workspace. Alternatively, anatomical features of the patient which can be pinpointed on both the visual images and the volume scans may be used.

The computations for alignment of the two frameworks and transformation of coordinates from one framework to the other use a linear algebra approach as described in theory and algorithmic solution in standard mathematical texts. Following alignment of the volume scan framework with the workspace framework, coordinates in the workspace framework are determined for one or more medical target(s) in the workspace.

Figure 6:
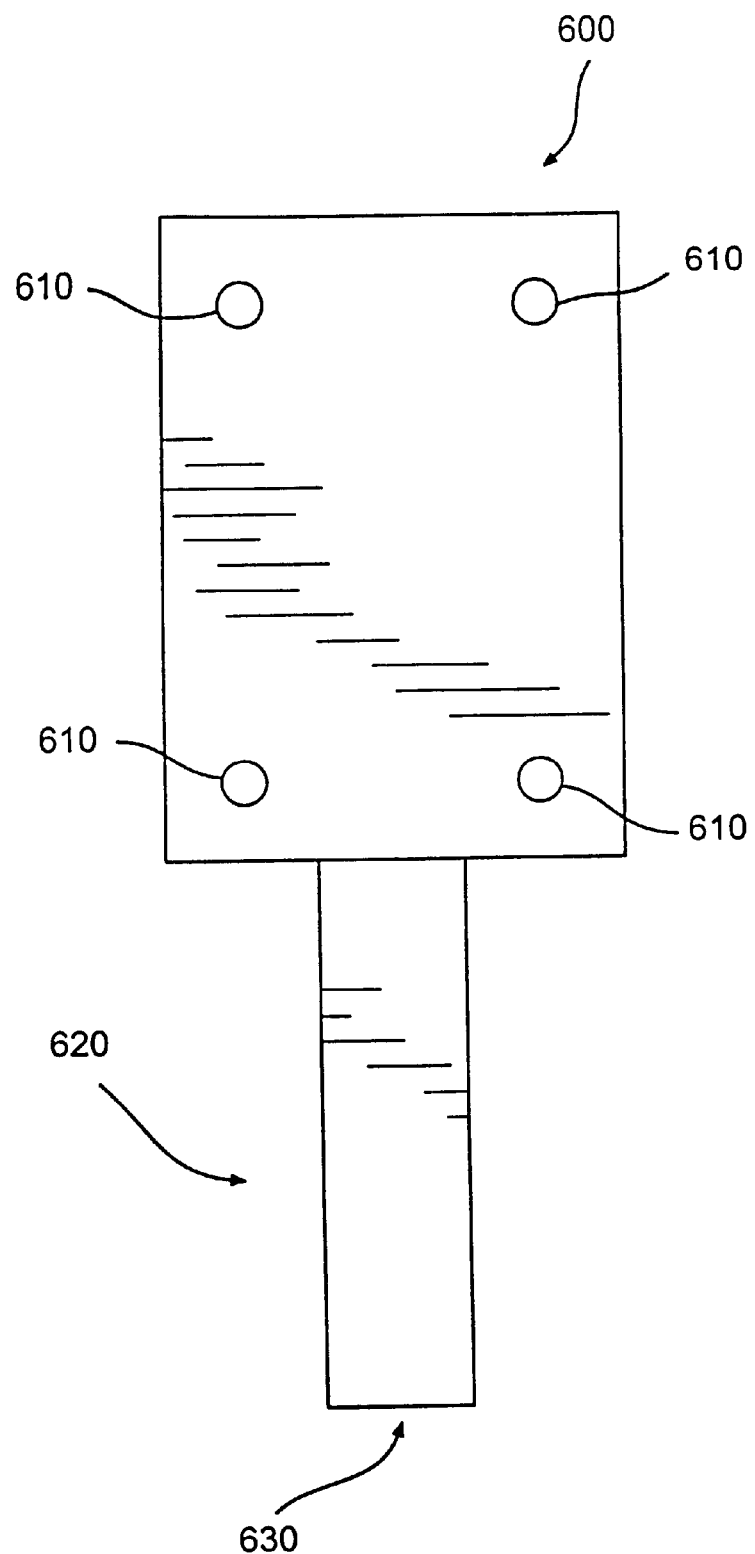
FIG. 6 shows a top plan view of a medical instrument.

Referring to FIG. 6, a medical instrument 600 to be used in the procedure is provided with at least two fiducial marks 610 which are visible to both cameras during the procedure. The physical distance between at least one of the instrument fiducial marks 610 and the significant or operative portion(s) of the instrument whose position it is desired to monitor, must be known. Such an operative portion 620 might, for example, be a surgical instrument (such as the cutting tip of a scalpel), pointer, electrodes, or a tip of a medical probe. In the next step of the method, the locational coordinates in the workspace framework of the instrument fiducial marks 610 are determined. From these coordinates and the known physical distance between one of the instrument fiducial marks 620 and the tip 630 of the instrument, the coordinates of the location of the instrument tip 630 are determined. The location of the instrument tip 630 relative to the location of the target is thereby established.

The position of the instrument including the tip, relative to the target and other structures within the workspace is then displayed for viewing by the person guiding the instrument. Optionally, from the line constituted by the two instrument fiducial marks, the path of the instrument if it moves further along that line from its present position is extrapolated to determine whether it will approach a desired target whose workspace coordinates are known.

To guide the instrument tip to the desired target, a navigational procedure analogues to the landing of an aircraft on a runway is performed. The workspace instrument is moved, and the positions of the instrument and its tip are displayed relative to the target. As necessary, the direction of travel of the instrument is adjusted, the path in the new direction is extrapolated, the instrument tip is moved and its location again determined. With sufficient speed in computation, it is expected that the system will be able to provide monitoring and navigation on a time-scale approaching or substantially reaching real-time. Such a real-time system would be highly preferred.

Table I presents results of accuracy tests of the localization apparatus and system. The tests were performed by comparing the 3D location coordinates derived using the video system with three-dimensional coordinates obtained by physical measurement with a calibrated Brown-Roberts-Wells (BRW) arc and a mockup of a patient's head.

TABLE I

TEST OF VIDEO LOCALIZER DEFINED
TARGET COMPARED TO ACTUAL TARGET
AND BRW LOCALIZER DEFINED TARGET

| ACTUAL STEREOTACTIC COORDINATE | BRW LOCALIZER STEREOTACTIC COORDINATE | VIDEO LOCALIZER STEREOTACTIC COORDINATE |
| --- | --- | --- |
| TARGET TEST 1 | | |
| AP = 92.6 | AP = 91.2 | AP = 92.0 |
| LAT = −6.8 | LAT = −6.5 | LAT = −5.8 |
| VERT = 14.0 | VERT = 14.9 | VERT = 13.2 |
| TARGET TEST 2 | | |
| AP = −16.0 | AP = −15.7 | AP = −17.8 |
| LAT = 25.0 | LAT = 24.2 | LAT = 26.1 |
| VERT = 48.4 | VERT = 48.1 | VERT = 48.4 |

As indicated by the data in Table 1, the localization results presently obtained with a working embodiment of the invented system are accurate to within at least about 2 millimeters of the locations determined by a conventional BRW localization system.

The system, comprising the apparatus and method for localization, may also be applied to localize and track features responsive to a neuron-stimulating electrode. Such a use is advantageous when the surgeon is attempting to navigate around essential structures such as the speech center in the brain, or to locate or confirm the location of a lesion causing a defect in neural functioning.

A method for using the guidance system to identify a neural lesion in terms of a functional deficit includes the following steps. After the workspace coordinate framework is established and the patient's head is positioned in the workspace and readied for the procedure, an electrode is moved slowly or at selected intervals from one position on the surface of the brain to another. At each position the electrode is activated to stimulate a response. When a functional deficit in the response is observed, the electrode path into the brain is extrapolated for a sufficient distance beyond the electrode tip, to reach the suspected depth of the lesion. The extrapolation is done from at least two fiducial marks associated with the electrode to define its direction. The extrapolated path is presumed to intersect the lesion causing the functional deficit. Movement of the electrode is repeated until at least one more, and desirably two more, surface positions which cause a similar functional deficit are found. A process similar to triangulation is used to determine the location of the lesion from the two or three extrapolated paths.

A process similar to the above may be used to identify a critical area such as a speech center which the surgeon wishes to avoid damaging. The major difference is that instead of extrapolating the electrode path from points where a functional deficit is observed, points where electrode stimulation causes activation of speech in the patient are used for the extrapolation.

Still other uses for the localization apparatus and method include: identifying the position of an ultrasound probe during an ultrasound scan of a segment of the brain (or other body region); identifying the position of the operative portions of an endoscope, fluoroscope, operating microscope, or the like, during procedures performed with such instruments.

The invention has been described primarily with reference to neurosurgical procedures wherein the medical workspace is the patient's head and brain. However, the technique may also be applied to other medical procedures where precise localization and guidance of medical instruments are desirable. These include plastic surgery, particularly of face and hands, and procedures involving the spine and spinal cord regions.

Moreover, the apparatus (including the fiducial structure) and method are not restricted to uses in a medical or surgical arena, but may further be applied to any procedure in which it is desired to correlate position information which would be available from 2D images of a workspace (either visual or X-ray images), with 3D position data describing interior and/or unseen regions of the workspace.

The invention provides numerous advantages for localization during surgical and other medical procedures. The invention is relatively inexpensive to practice, since the method can be performed with a commercially available computer workstation, and/or an apparatus including such a workstation or even a so-called personal computer as the computing means. No cumbersome frame is required to be attached to the patient, as in devices of the BRW type. The system provides free hand tracking of a medical instrument during a procedure, e.g. the instrument's position can be determined without requiring that it be attached to a reference structure such as the BRW ring or any other mechanical device.

Moreover, as long as the image pairs are made from the same respective locations as the calibration image pair, nearly any feature in the workspace can be accurately localized in terms of the workspace coordinate framework. If it is desired to select new locations for making the image pairs, to provide a better view of portions of the workspace or any other reason, all that need be done is to reposition the fiducial structure in the workspace to make a new pair of calibration images. The computing means then can readily compute a new workspace framework, the fiducial structure can be removed and the medical procedure continued with a relatively short delay. These and other advantages will be apparent to those in the medical arts.

In a further embodiment, the computing means 232 is configured to "recognize" a selection of medical or surgical instruments and appliances. This recognition is achieved by configuring computing means 232 with algorithms for edge detection, color recognition or both, and by including in its nonvolatile memory data correlating the detected shape and color patterns with those of selected instruments. When a particular instrument is held in the workspace so as to be clear of significant obstructions and an image pair is made, computing means 232 then can "recognize" the instrument. Highly desirably, computing means 232 further provides monitor-screen and/or voice notification of the identity of the instrument.

Subsequently, during use of the instrument, computing means 232 tracks the position of the instrument and of the cutting tip or other relevant portion, relative to the features in the workspace such as the patient's body part. This tracking is accomplished by using the edge and/or color detection algorithms for portions of the instrument which are visible in both images of the image pair, in combination with extrapolation of the position and direction of portions of the instrument not visible in the image pair. In other words, the computing means is also operable, having once "recognized" an instrument, to recognize certain locations on the instrument and to extrapolate the coordinates of an unseen portion such as a cutting tip, from the identified position of one or more first locations. The computing means also provides information via screen and/or voice notification, of the position of the operative portion of the instrument relative to that of structures of interest in the workspace.

Figure 5:
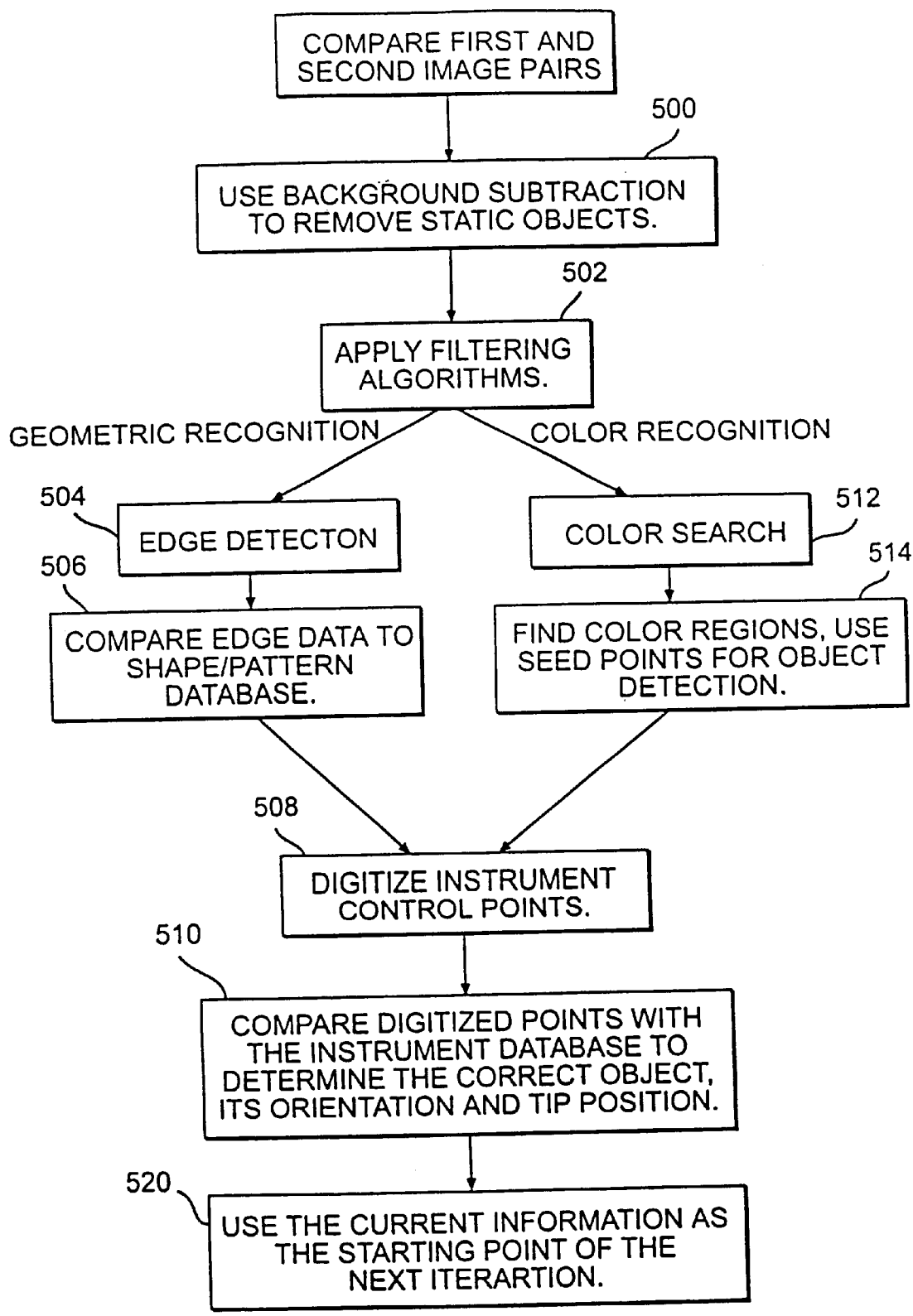
FIG. 5 is a flow chart of a portion of the operation of a further embodiment in which the control means is configured to provide object recognition and location of medical instruments and the like in the image field.

FIG. 5 illustrates generally the internal operation of a computing means so configured. First, a digitized image pair made prior to the introduction of the instrument into the workspace is compared to an image pair made with the instrument in substantially complete view, and background subtraction is used to remove static objects in the image field (step 500). Methods and algorithms for this procedure are known from movie compression. Preferably, when the instrument is first brought into the workspace it is held clear of any obstructions so as to be readily visible in both images of an image pair.

Next, filtering algorithms are applied to sharpen the image and enhance object edges (step 502). Many kinds of filtering algorithms are known in the art: a survey of filtering methods can be found in *Computer Graphics: principles and Practice* (2nd Edition) by J. D. Foley, A. van Dam, S. K. Feiner, and J. F. Hughes, Addison-Wesley Publ., Reading, Mass. (1990).

After the image has been appropriately filtered, one or both of two recognition protocols, one based on edge detection and one on color detection, are applied.

In an edge detection protocol (steps 504, 506), an algorithm for edge detection is used to define the edges of the instrument and a geometrical comparison is made to match the shape of the instrument to shapes of selected instruments stored in the memory. Once the instrument is identified (a match is found), a series of control points on the instrument are digitized (step 508) and its orientation and tip position are determined in terms of coordinates in the 3D workspace (step 510). This process may be accomplished by defining the instrument with a series of three views from different angles using a grid derived from a solid sphere or other conventional 3-dimensional shape.

If color recognition is used, it will usually be necessary to provide the instruments with colored markers. A color recognition sequence (steps 512, 514) includes a color search to match the color to colors in the database for selected instruments, followed by use of seed points within colored areas to achieve object recognition. Once an object is matched to an instrument in the database, the remaining steps 508, 510 are performed as described in the preceding paragraph.

Techniques for edge detection, geometric matching, and color recognition protocols are known in the art; it is not important which specific techniques are used so long as the results are accurate and can be obtained in time approaching real time with a reasonable amount of processing capacity.

In tracking a surgical procedure, the next step 520 is to repeat steps 500–510 and 512–514 as long as desired, using the information on identity and position of the instrument in each image pair as a starting point for analysis of the next image pair.

The surgical instruments need not have special fiduciary or other marks unless color recognition is to be used. If colored or other markers are used with the instruments, these are desirably located to be readily visible to both cameras in the workspace and not easily obscured by the physician's hand, etc. In the initial recognition sequence, it may be desirable to provide image pairs of each instrument in three different orthogonal positions in order to fully capture its dimensions and shape. A "wire model" may then be computationally constructed to define the relative coordinates of points on the instrument.

While the computations and computational sequences have been described with respect to a particular working embodiment, it will be recognized by those of skill in the arts of computing and image projection that there are many alternate types of computations and computational sequences that may be used to accomplish essentially the same result in the same or similar way. For example, algorithms for implementation of a least squares approach are many, as problem solving techniques vary and grow within the field of numerical analysis. Also, alternate projection computation methods besides that of Bopp and Krauss referenced herein, may be applied to solve the problem of mapping from a pair of 2D images to a 3D spatial framework.

It will also be apparent that other configurations of the components of the apparatus are possible and are functional to practice the invention. It will further be apparent that the precise components of the apparatus can be varied, without departing from the spirit and concept of the invention. The claims alone define the scope of the invention.

What is claimed is:

1. A method for determining a position of a region of interest of an anatomy, comprising:
   providing volume scan data representative of an anatomy;
   establishing a medical workspace, which includes the anatomy, using a pair of cameras calibrated to each other;
   identifying portions of the anatomy through selective illumination of the anatomy;
   computing positions of the identified portions with respect to the medical workspace;
   deriving a relationship between the medical workspace and the volume scan data using the computed positions of the identified portions; and
   determining a position of a region of interest in the medical workspace using the relationship and the volume scan data.

2. The method of claim 1, wherein the pair of cameras acquire 2D data along differing sightlines, and wherein the method further comprises computing a 3D coordinate framework of the medical workspace utilizing the 2D data.

3. The method of claim 2, further comprising:
   projecting light onto a plurality of locations on a surface of the anatomy;
   detecting the plurality of locations by the cameras; and
   computing the 3D positions of the plurality of locations in the 3D coordinate framework of the medical workspace.

4. The method of claim 3, wherein the projecting includes projecting a light grid onto the surface of the anatomy.

5. The method of claim 3, further comprising:
   computing a transform to align the 3D coordinate framework of the medical workspace to a 3D coordinate framework of the volume scan, wherein the computing of the transform includes using the plurality of locations described in the 3D coordinate framework of the medical workspace and the 3D coordinate framework of the volume scan; and
   applying the transform to the position of the region of interest, described in the 3D coordinate frame work of the volume scan data, to obtain the 3D position of the region of interest in the medical workspace.

6. The method of claim 3, wherein the projecting includes projecting a laser light to provide a plurality of light spots on the surface of the anatomy.

7. The method of claim 6, further comprising selecting the locations on the surface of the anatomy manually.

8. The method of claim 6, further comprising selecting the locations on the surface of the anatomy automatically by a computing means.

9. The method of claim 1, further comprising:
   removably placing a fiducial structure within the medical workspace; and
   acquiring data relating to the medical workspace containing the fiducial structure.

10. The method of claim 9, wherein the fiducial structure includes a plurality of markers arranged to define a 3D coordinate reference.

11. The method of claim 1, further comprising:
    determining the position of a medical instrument in the medical workspace; and
    comparing the position of the medical instrument with the position of the region of interest.

12. The method of claim 11, further comprising displaying a representation of the medical instrument in relation to the region of interest.

13. The method of claim 11 wherein the medical instrument includes a fluoroscope.

14. The method of claim 11 further comprising determining the workspace coordinates of the medical instrument through color recognition.

15. The method of claim 14 further comprising determining the workspace coordinates of the medical instrument based upon the color of markers positioned on the medical instrument.

16. The method of claim 11 further comprising determining the workspace coordinates of the medical instrument based on geometric matching.

17. The method of claim 11 further comprising using pattern recognition data to recognize the medical instrument from a plurality of medical instruments.

18. The method as defined in claim 17 further comprising determining the pattern by detecting an edge of the medical instrument.

19. A method for determining a position of a medical instrument relative to a patient's anatomy, comprising:
    providing volume scan data representative of an anatomy;
    establishing a medical workspace using sensors;
    identifying portions of the anatomy through selective illumination of the anatomy;
    computing positions of the identified portions with respect to the medical workspace;
    deriving a relation between the medical workspace and the volume scan data using the computed positions of the identified portions;
    tracking the position of a medical instrument using the sensors; and
    aligning the position of a region of interest and the position of medical instrument by using the relation.

20. The method of claim 19, further comprising:
temporarily placing a fiducial structure within the medical workspace;
acquiring data of the medical workspace containing the fiducial structure using the sensors; and
removing the fiducial structure after the medical workspace is established.

21. The method of claim 20, wherein the fiducial structure includes a plurality of markers arranged to define a 3D coordinate reference.

22. The method of claim 19, wherein the sensors include two cameras acquiring 2D data from differing sightlines, and wherein the method further comprises computing a 3D coordinate framework of the medical workspace utilizing the 2D data and a projection algorithm.

23. The method of claim 22, further comprising:
projecting light from an illumination source to a plurality of locations on a surface of the anatomy;
detecting the plurality of locations by the cameras; and
computing the 3D positions of the plurality of locations in the 3D coordinate framework of the medical workspace.

24. The method of claim 23, wherein the illumination source is a light projector which projects a light grid onto the surface of the anatomy.

25. The method of claim 23, wherein the illumination source is a laser which projects a plurality of light spots onto the surface of the anatomy.

26. The method of claim 25, further comprising selecting the plurality of locations manually.

27. The method of claim 25, further comprising selecting the plurality of locations automatically with a computing means.

28. The method of claim 23, further comprising:
computing a transform to correlate the 3D coordinate framework of the medical workspace to a 3D coordinate framework of the volume scan data, wherein the computing of the transform includes using the plurality of locations described in the 3D coordinate framework of the medical workspace and the 3D coordinate framework of the volume scan data;
applying the transform to the position of the region of interest, described in the 3D coordinate framework of the volume scan data, to obtain the 3D position of the region of interest in the medical workspace; and
comparing the position of the region of interest and the position of the medical instrument in the 3D coordinate framework of the medical workspace.

29. The method of claim 19, further comprising displaying a representation of the medical instrument in relation to a representation of the region of interest.

30. The method of claim 19 further comprising determining the workspace coordinates of the medical instrument through color recognition.

31. The method of claim 30 further comprising determining the workspace coordinates of the medical instrument based upon the color of markers positioned on the medical instrument.

32. The method of claim 19 further comprising determining the workspace coordinates of the medical instrument based on geometric matching.

33. The method of claim 19 further comprising using pattern recognition data to recognize the medical instrument from a plurality of medical instruments.

34. The method as defined in claim 33 further comprising determining the pattern by detecting an edge of the medical instrument.

35. A method for determining the position of a medical instrument relative to a patient's anatomy within a medical workspace, comprising:
providing volume scan data representative of a patient's anatomy, the volume scan data having a first 3D coordinate framework;
arranging a first camera and a second camera along respective first and second sightlines of a medical workspace, wherein the first and second sightlines are arranged at an angle;
acquiring a first pair of images of the medical workspace, wherein each image of the first pair is acquired using the first and second video camera;
calibrating the first and second camera to each other and the medical workspace;
establishing a second 3D coordinate framework of the medical workspace utilizing the first pair of images;
illuminating a plurality of points on the surface of the patient's anatomy with a laser, the selection of the plurality of points being one of manual and automatic selection;
acquiring subsequent pairs of images of the medical workspace using the first and second cameras taken along the first and second sightlines, respectively, as used by the first pair of images;
computing the positions of the plurality of points in the second 3D coordinate framework using the subsequent image pairs;
deriving a correspondence between the first 3D coordinate framework and the second 3D coordinate framework;
providing pattern recognition data and medical instrument structure data corresponding to a plurality of different medical instruments;
recognizing a medical instrument from the plurality of different medical instruments, appearing in the subsequent image pairs, using the recognition and medical instrument structure data;
tracking a position of an operative portion of the medical instrument in the second 3D coordinate framework using the subsequent pairs of images;
determining a position of a region of interest in the second 3D coordinate framework, using the correspondence and a position of the region of interest described in the first 3D coordinate framework; and
comparing the positions of the operative portion of the medical instrument and the region of interest in the first 3D coordinate framework.

36. The method of claim 35, further comprising:
providing a fiducial structure within a medical workspace containing the patient's anatomy, wherein the fiducial structure includes a plurality of markers arranged to define a 3D coordinate system.

37. The method of claim 35 further comprising determining the workspace coordinates of the medical instrument through color recognition.

38. The method of claim 37 further comprising determining the workspace coordinates of the medical instrument based upon the color of markers positioned on the medical instrument.

39. The method of claim 35 further comprising determining the workspace coordinates of the medical instrument based on geometric matching.

40. The method of claim 35 further comprising using the pattern recognition data to recognize the medical instrument from a plurality of medical instruments.

41. The method as defined in claim 40 further comprising determining the pattern by detecting an edge of the medical instrument.

42. A method for determining the position of a medical instrument relative to a patient's anatomy within a medical workspace, comprising:

provsuming volume scan data representative of a patient's anatomy, the volume scan data having a first 3D coordinate framework;

providing a fiducial structure within a medical workspace containing the patient's anatomy, wherein the fiducial structure includes a plurality of markers arranged to define a 3D coordinate system;

arranging a first camera and a second camera along respective first and second sightlines of a medical workspace, wherein the first and second sightlines are arranged at an angle;

acquiring a first pair of images of the medical workspace containing the fiducial structure, wherein each image of the first pair is acquired using the first and second cameras;

calibrating the first and second cameras to each other and the medical workspace;

establishing a second 3D coordinate framework of the medical workspace containing the fiducial structure utilizing the first pair of images;

illuminating a plurality of points on the surface of the patient's anatomy with a laser, the selection of the plurality of points being one of manual and automatic selection;

acquiring subsequent pairs of images of the medical workspace using the first and second cameras taken along the first and second sightlines, respectively, as used by the first pair of images;

computing the positions of the plurality of points in the second 3D coordinate framework using the subsequent image pairs;

deriving a correspondence between the first 3D coordinate framework and the second 3D coordinate framework;

providing pattern recognition data and medical instrument structure data corresponding to a plurality of different medical instruments;

recognizing a medical instrument from the plurality of different medical instruments, appearing in the subsequent image pairs, using the recognition and medical instrument structure data;

tracking a position of an operative portion of the medical instrument in the second 3D coordinate framework using the subsequent pairs of images;

determining a position of a region of interest in the second 3D coordinate framework, using the correspondence and a position of the region of interest described in the first 3D coordinate framework; and comparing the positions of the operative portion of the medical instrument and the region of interest in the first 3D coordinate framework.

43. The method of claim 42 further comprising determining the workspace coordinates of the medical instrument through color recognition.

44. The method of claim 43 further comprising determining the workspace coordinates of the medical instrument based upon the color of markers positioned on the medical instrument.

45. The method of claim 42 further comprising determining the workspace coordinates of the medical instrument based on geometric matching.

46. The method of claim 42 comprising using the pattern recognition data to recognize the medical instrument from a plurality of medical instruments.

47. The method as defined in claim 46 further comprising determining the pattern by detecting an edge of the medical instrument.

* * * * *